(12) United States Patent
Isobe et al.

(10) Patent No.: US 12,599,289 B2
(45) Date of Patent: Apr. 14, 2026

(54) ENDOSCOPE

(71) Applicant: OLYMPUS MEDICAL SYSTEMS CORP., Tokyo (JP)

(72) Inventors: Yosuke Isobe, Nishitokyo (JP); Takeo Suzuki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 616 days.

(21) Appl. No.: 17/971,749

(22) Filed: Oct. 24, 2022

(65) Prior Publication Data

US 2023/0126521 A1     Apr. 27, 2023

Related U.S. Application Data

(60) Provisional application No. 63/271,303, filed on Oct. 25, 2021.

(51) Int. Cl.
| | |
|---|---|
| *A61B 1/00* | (2006.01) |
| *A61B 1/005* | (2006.01) |

(52) U.S. Cl.
CPC ...... *A61B 1/00098* (2013.01); *A61B 1/00103* (2013.01); *A61B 1/00128* (2013.01); *A61B 1/0052* (2013.01); *A61B 1/0057* (2013.01)

(58) Field of Classification Search
CPC ............ A61B 1/00042; A61B 1/00098; A61B 1/0052; A61B 1/0057
See application file for complete search history.

(56) References Cited

U.S. PATENT DOCUMENTS

| | | | | |
|---|---|---|---|---|
| 4,706,655 A | * | 11/1987 | Krauter ................. | A61B 1/313 600/153 |
| 5,460,168 A | * | 10/1995 | Masubuchi ........ | A61B 1/00098 600/107 |
| 7,341,555 B2 | | 3/2008 | Ootawara et al. | |
| 2007/0282167 A1 | * | 12/2007 | Barenboym ......... | A61B 1/0052 600/131 |
| 2015/0148598 A1 | * | 5/2015 | Fukushima ........ | A61B 1/00098 600/109 |

(Continued)

FOREIGN PATENT DOCUMENTS

| | | | |
|---|---|---|---|
| JP | H07313446 A | * | 12/1995 |
| JP | H08-126644 A | | 5/1996 |

(Continued)

*Primary Examiner* — Michael J Carey
*Assistant Examiner* — Stephen Floyd London
(74) *Attorney, Agent, or Firm* — Morgan, Lewis & Bockius LLP

(57) ABSTRACT

An endoscope comprising: an insertion portion; a raising base provided at a distal end of the insertion portion; a wire configured to move in a raising direction to raise the raising base; a biasing element attached to the wire and configured to apply to the wire a biasing force in the raising direction; and an operation portion coupled to a proximal end of the insertion portion, the operation portion including a switching mechanism having a first state and a second state. The switching mechanism is configured to switch between the first state and the second state. In the first state, the switching mechanism prevents the biasing force from moving the wire in the raising direction and, in the second state, the switching mechanism allows the biasing force to move the wire in the raising direction.

19 Claims, 8 Drawing Sheets

(56)  References Cited

U.S. PATENT DOCUMENTS

| | | | | |
|---|---|---|---|---|
| 2016/0231556 A1* | 8/2016 | Yasunaga | ........... | G02B 23/2476 |
| 2017/0000316 A1* | 1/2017 | Sueyasu | ............. | A61B 1/00098 |
| 2017/0215704 A1* | 8/2017 | Tsumaru | ........... | A61B 1/00128 |
| 2021/0315445 A1* | 10/2021 | Wilder | ................ | A61B 1/0058 |
| 2022/0202278 A1* | 6/2022 | Melito | ............... | A61B 1/00042 |
| 2023/0157523 A1* | 5/2023 | Teatini | .............. | A61B 1/00098 |
| | | | | 600/107 |
| 2023/0233062 A1* | 7/2023 | Harada | ............. | A61B 1/00098 |
| | | | | 600/107 |
| 2023/0337894 A1* | 10/2023 | Dhanotiya | ........... | A61B 1/0052 |
| 2023/0389785 A1* | 12/2023 | Inoue | ................ | A61B 1/00042 |

FOREIGN PATENT DOCUMENTS

| | | | |
|---|---|---|---|
| JP | 3368568 | B2 | 1/2003 |
| JP | 4716594 | B2 | 7/2011 |
| JP | 2013-000179 | A | 1/2013 |
| JP | 2020-089598 | A | 6/2020 |

* cited by examiner

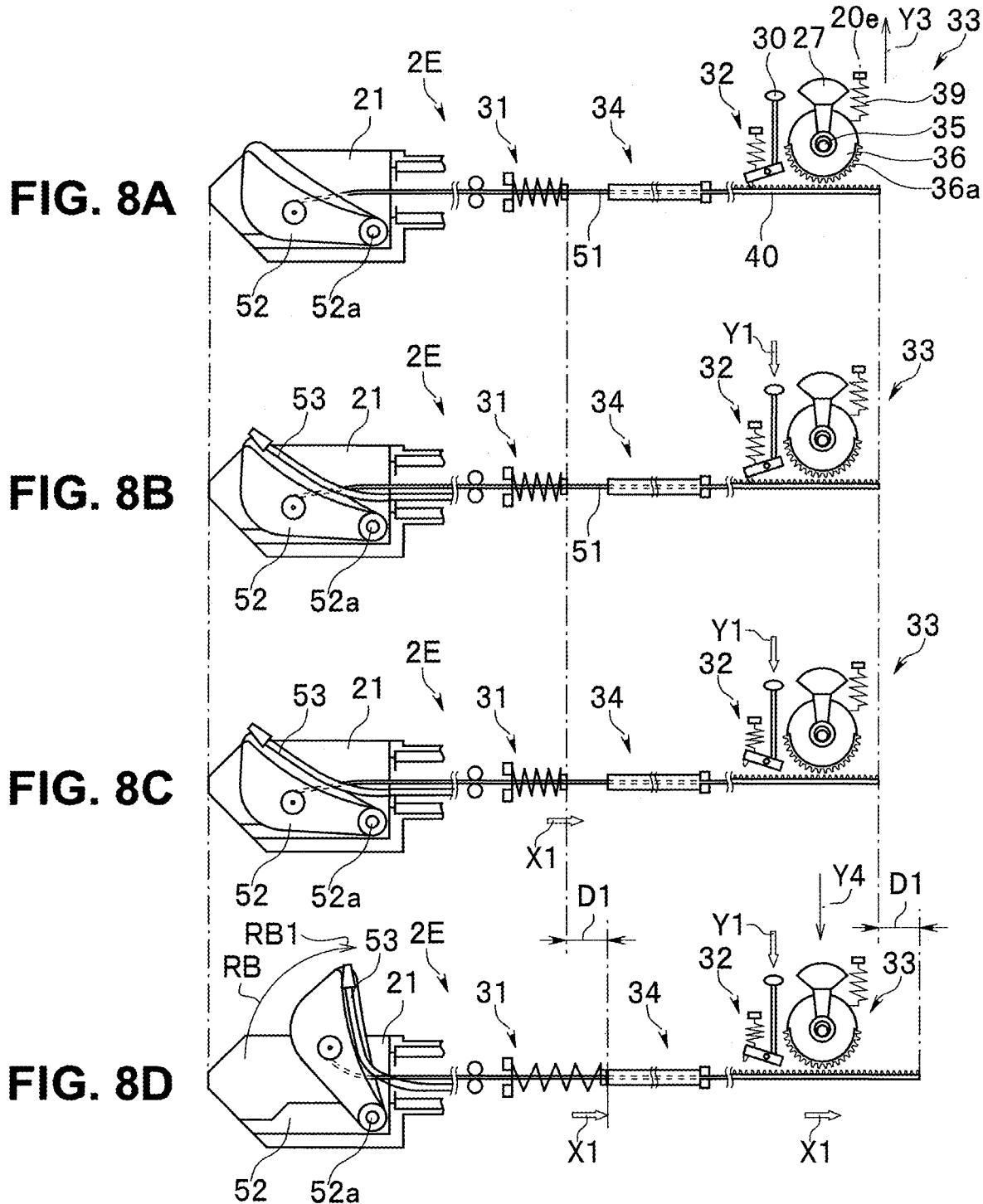

ENDOSCOPE

RELATED APPLICATION DATA

This application is based on and claims priority under 35 U.S.C. § 119 to U.S. Provisional Application No. 63/271, 303 filed on Oct. 25, 2021, the entire contents of which are incorporated herein by reference.

FIELD OF THE DISCLOSURE

The present disclosure relates to an endoscope including a treatment-instrument raising base (forceps elevator).

BACKGROUND

Conventionally, an endoscope has been widely used in, for example, medical and industrial fields. A medical endoscope used in the medical field has a function to acquire an image of, for example, a lesion part inside an organ or the like by inserting an insertion portion including an image pickup unit into a body cavity of a living body. Then, observation and examination of, for example, the lesion part are performed based on the acquired image. An industrial endoscope used in the industrial field has a function to acquire an image of flaw, corrosion, or the like inside, for example, a device or a machine facility such as a jet engine or a factory pipe by inserting an insertion portion including an image pickup unit into the device or the facility. Then, observation and examination of flaw, corrosion, or the like inside the device or the facility are performed based on the acquired image.

For example, Japanese Patent Application Laid-Open Publication No. 2020-89598 has recently disclosed a medical endoscope including a treatment-instrument raising base for directing, toward a desired lesion part or the like, a treatment instrument inserted into a body cavity.

In the endoscope disclosed by the above-described Japanese Patent Application Laid-Open Publication No. 2020-89598 or the like, a raising operation of the treatment-instrument raising base is performed through an operation to incline a treatment instrument raising lever provided at an operation portion of the endoscope so that a pulling wire is moved forward and backward through a raising-base operation mechanism.

The raising-base operation mechanism includes a rotation plate configured to rotate as the treatment instrument raising lever is inclined. A pulling member of a link mechanism is connected to the rotation plate. The link mechanism converts rotation motion of the rotation plate into linear motion of the pulling member. The pulling wire is connected to the pulling member. The treatment-instrument raising base is connected to a distal end of the pulling wire. With this configuration, the raising base can be operated.

SUMMARY OF THE DISCLOSURE

An endoscope comprising: an insertion portion; a raising base provided at a distal end of the insertion portion; a wire configured to move in a raising direction to raise the raising base; a biasing element attached to the wire and configured to apply to the wire a biasing force in the raising direction; and an operation portion coupled to a proximal end of the insertion portion, the operation portion including a switching mechanism having a first state and a second state. The switching mechanism is configured to switch between the first state and the second state. In the first state, the switching mechanism prevents the biasing force from moving the wire in the raising direction and, in the second state, the switching mechanism allows the biasing force to move the wire in the raising direction.

BRIEF DESCRIPTION OF THE DRAWINGS

FIG. 8A is a diagram illustrating a first-half part of a configuration and an effect of a third modification of the endoscope according to the embodiment of the present disclosure.

FIG. 8B is a diagram illustrating the first-half part of the configuration and the effect of the third modification of the endoscope according to the embodiment of the present disclosure.

FIG. 8C is a diagram illustrating the first-half part of the configuration and the effect of the third modification of the endoscope according to the embodiment of the present disclosure.

FIG. 8D is a diagram illustrating the first-half part of the configuration and the effect of the third modification of the endoscope according to the embodiment of the present disclosure.

DETAILED DESCRIPTION

Figure 1:
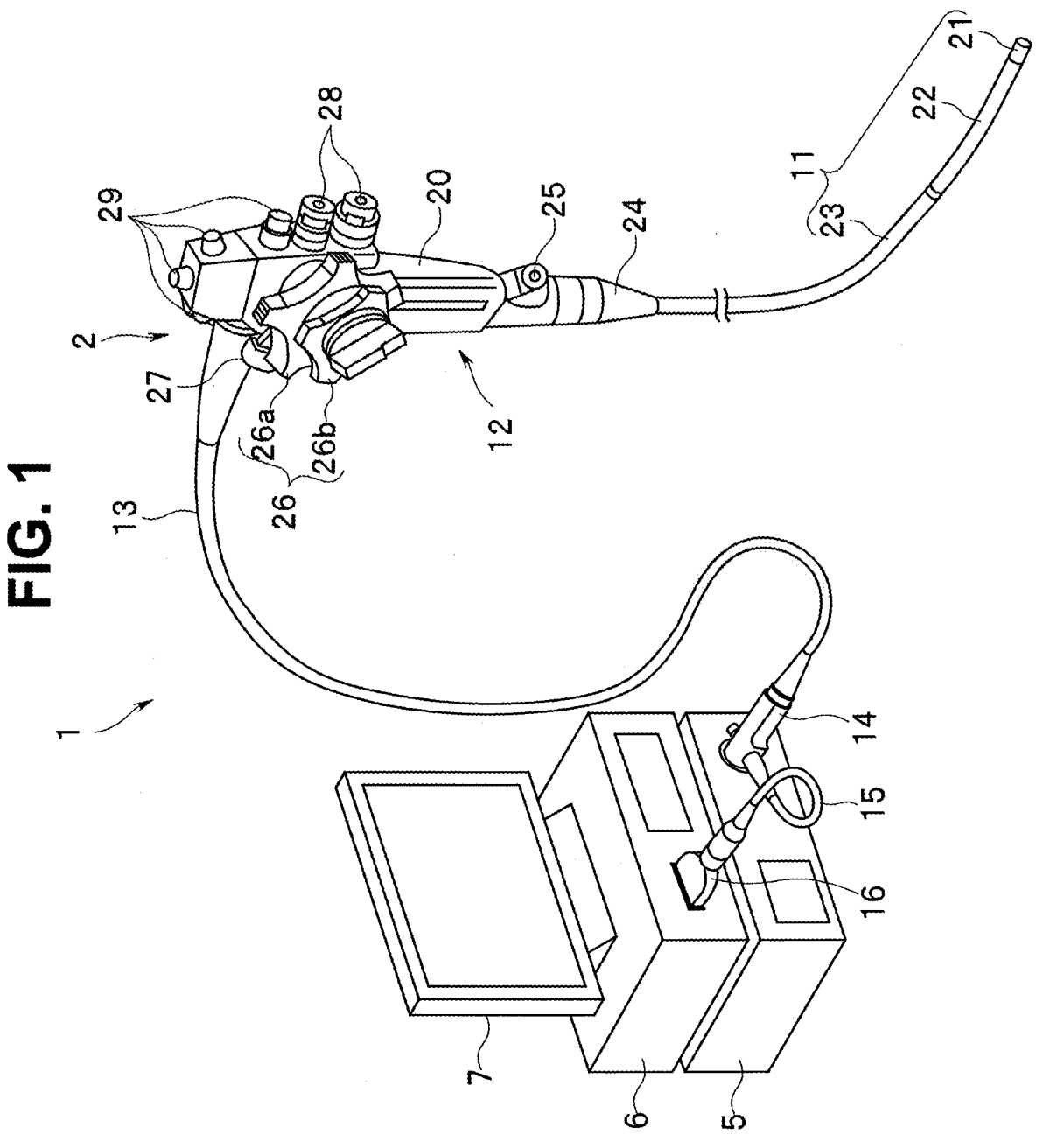
FIG. 1 is a schematic configuration diagram illustrating an endoscope system including an endoscope according to an embodiment of the present disclosure.

Typically, operations of a bending portion and a treatment-instrument raising base of a conventional endoscope are performed by an endoscope operator manually operating various operation members (such as a rotation knob and a lever member) provided at an operation portion. Specifically, the endoscope operator performs a bending operation of the bending portion by, for example, performing a rotational operation of a bending knob by using fingers of a left hand while holding the operation portion of the endoscope with the left hand. In this case, an operation state of a bending operation knob needs to be maintained to maintain a bending state. For example, to continue observation of a lesion part or the like by an image pickup unit at an endoscope distal end portion, it can maintain an orientation of the image pickup unit by maintaining the bending state of the bending portion.

In a certain situation, a treatment instrument is operated while the bending state of the bending portion is maintained. In this case, the treatment-instrument raising base is operated by operating an operation member different from the bending operation knob to direct the treatment instrument toward a lesion part or the like while maintaining the bending state of the bending portion.

Thus, in such a situation, the endoscope operator needs to simultaneously operate a plurality of operation members. In this case, each operation member has, for example, state restorability and it can continuously apply a predetermined amount of force to each operation member to maintain an operation state. Accordingly, further improvement of operability of the endoscope is required.

According to an embodiment of the present disclosure described below, it is possible to provide an endoscope that can reduce an amount of operational force on a raising lever for raising the treatment-instrument raising base and cumbersomeness of operability and can contribute to reduction of a load applied on the endoscope operator at raising-base operation.

The present disclosure will be described below with reference to an illustrated embodiment. Each drawing used in the following description is schematically illustrated, and dimensional relations, scaling, and the like among members are illustrated differently for each constituent component in some cases to indicate the constituent component in a size enough to allow recognition on the drawing. Thus, in the present disclosure, for example, the number of constituent components illustrated in each drawing, a shape of each constituent component, a size ratio of the constituent components, and a relative positional relation among the constituent components are not limited to illustrated forms.

First, a schematic configuration of an endoscope system including an endoscope according to the embodiment of the present disclosure will be described below with reference to FIG. 1.

As illustrated in FIG. 1, an endoscope system 1 including an endoscope according to the embodiment of the present disclosure mainly includes an endoscope 2, a light source device 5, a video processor 6, and a color monitor 7. Note that the endoscope 2, the light source device 5, the video processor 6, and the color monitor 7 are electrically connected to each other through a connection cable or the like (partially not illustrated).

The endoscope 2 includes an insertion portion 11, an operation portion 12, and a universal code 13.

The insertion portion 11 is an elongated pipe-shaped constitutional unit that is inserted into a subject. The insertion portion 11 is constituted by, sequentially from a distal end side (one end side), a distal end portion 21, a bending portion 22, and a flexible tube portion 23 continuously connected to each other. For example, a distal end opening portion, an observation window, a plurality of illumination windows, an observation window cleaning port, and an observation object cleaning port, which are not illustrated, are disposed on a distal end surface of the distal end portion 21.

An image pickup unit (not illustrated) included in the distal end portion 21 is disposed on a back side of the observation window. An end face of a light guide bundle is provided on the back side of the plurality of illumination windows. The light guide bundle is an illumination light transmission member that transmits illumination light from the light source device 5. The light guide bundle is disposed from the distal end portion 21 to an end part of the universal code 13 by insertion. In addition, a treatment-instrument insertion channel that allows insertion of a treatment instrument and the like is inserted inside the insertion portion 11.

The operation portion 12 includes a bend preventing portion 24, a forceps port 25, an operation portion body 20, a bending operation member 26, a raising operation lever 27, a switching operation member 30 (not illustrated in FIG. 1), various switches 28, and image pickup switches 29. Although described later in detail, various mechanisms (raising-base-related mechanism units (31, 32, 33, and 34)) for operating a treatment-instrument raising base 52 (refer to FIG. 2; hereinafter simply referred to as a raising base 52) to be described later are included inside the operation portion 12. The operation portion 12 is coupled to a proximal end of the insertion portion 11.

The operation portion 12 is coupled on a proximal end side (other end side) of the insertion portion 11. The bend preventing portion 24 is provided at a site to which a proximal end of the insertion portion 11 is connected. Accordingly, the bend preventing portion 24 plays a role to protect bending of a proximal end part of the insertion portion 11 extending from the operation portion 12.

The forceps port 25 is an opening part on the operation portion 12 side, which communicates with the treatment-instrument insertion channel (not illustrated) of the operation portion 12. The forceps port 25 is disposed at a side part near a distal end of the operation portion 12.

The operation portion body 20 is a component including various structural objects inside and having a function as a grip portion for grasping the endoscope 2.

The bending operation member 26 is a rotational operation member for performing a bending operation of the bending portion 22. The bending operation member 26 includes, for example, two bending operation knobs 26a and 26b. The bending portion 22 can be operated to bend upward, downward, rightward, and leftward with respect to an insertion axis through rotational operation of the two bending operations 26a and 26b.

The raising operation lever 27 is an operation member that acts on a raising-base lay-down operation mechanism 33 (refer to FIG. 2) to be described later to perform a lay-down operation of the raising base 52 (refer to FIG. 2) to be described later. The switching operation member 30 is an operation member that acts on a switching mechanism 32 (refer to FIG. 2) to be described later to switch a state of the raising base 52. Note that configurations and effects of the raising operation lever 27 and the switching operation member 30 will be described later in detail. The operation portion 12 includes the switching mechanism 32 having a first state and a second state, the switching mechanism is configured to switch between the first state and the second state. In the first state, the switching mechanism 32 prevents the biasing force from moving the wire in the raising direction and, in the second state, the switching mechanism allows the biasing force to move the wire in the raising direction. The operation portion 12 includes a raising base operator 27 and a coupling unit 33. The raising base operator 27 that is movable between a first position and a second position. The coupling unit 33 is attached to a pulling wire 51 and the raising base operator 27 is in engagement with the coupling unit 33. When the switching mechanism 32 is in the second state, movement of the raising base operator 27 toward the first position moves the pulling wire 51 in a direction opposite of the raising direction. A first end of the pulling wire 51 is connected to the raising base 52 and the pulling wire 51 extends from the raising base 52 to the operation portion 12, and the raising base 52 is raised by movement of the pulling wire 51 in the raising direction and the raising base 52 is lowered by movement of the wire in a direction opposite of the raising direction.

The switches 28 are operation members corresponding to, for example, a gas feeding operation, a liquid feeding operation, and a suction operation. The image pickup switches 29 are operation members that are mainly operated to perform an image pickup function such as a zooming function.

The universal code 13 is a composite cable extending from the operation portion 12. A light source connector 14 is connected to a distal end of the universal code 13. An electrical cable 15 extends from the light source connector 14. An electrical connector 16 is connected to a distal end of the electrical cable 15. The light source connector 14 is connected to a front surface panel of the light source device 5. The electrical connector 16 is also connected to a front surface panel of the video processor 6. Note that the raising base 52 (not illustrated in FIG. 1; refer to FIG. 2) is included in the distal end portion 21. Accordingly, the raising base 52 is provided on the one end side of the insertion portion 11. The raising base 52 is a constitutional member for changing, to a direction in a predetermined range, a leading direction of a treatment instrument 53 (not illustrated in FIG. 1; refer to FIG. 2) introduced through the forceps port 25 of the operation portion 12, inserted into the treatment-instrument insertion channel (not illustrated) of the insertion portion 11, and led out of the distal end portion 21. Configurations and effects of the raising base 52 will be described later in detail. Note that connection to a control instrument having functions of the light source device 5 and the video processor 6 may be achieved by a connector having integrated functions of a light source connector and an electrical connector.

Note that the endoscope 2 according to the present embodiment is, for example, a duodenum endoscope, a biliary-tract endoscope, or an ultrasound endoscope including an ultrasound probe configured to transmit and receive ultrasound inside of the distal end portion 21 of the insertion portion 11. The endoscope 2 is, for example, a single-use endoscope that is discarded (disposed of) after used once.

Subsequently, configurations of the raising base 52 and the raising-base-related mechanism units (a biasing force generation mechanism 31, the switching mechanism 32, the raising-base lay-down operation mechanism 33, and a drive power transmission mechanism 34) in the endoscope 2 according to the present embodiment will be described below mainly with reference to FIG. 2.

Figure 2:
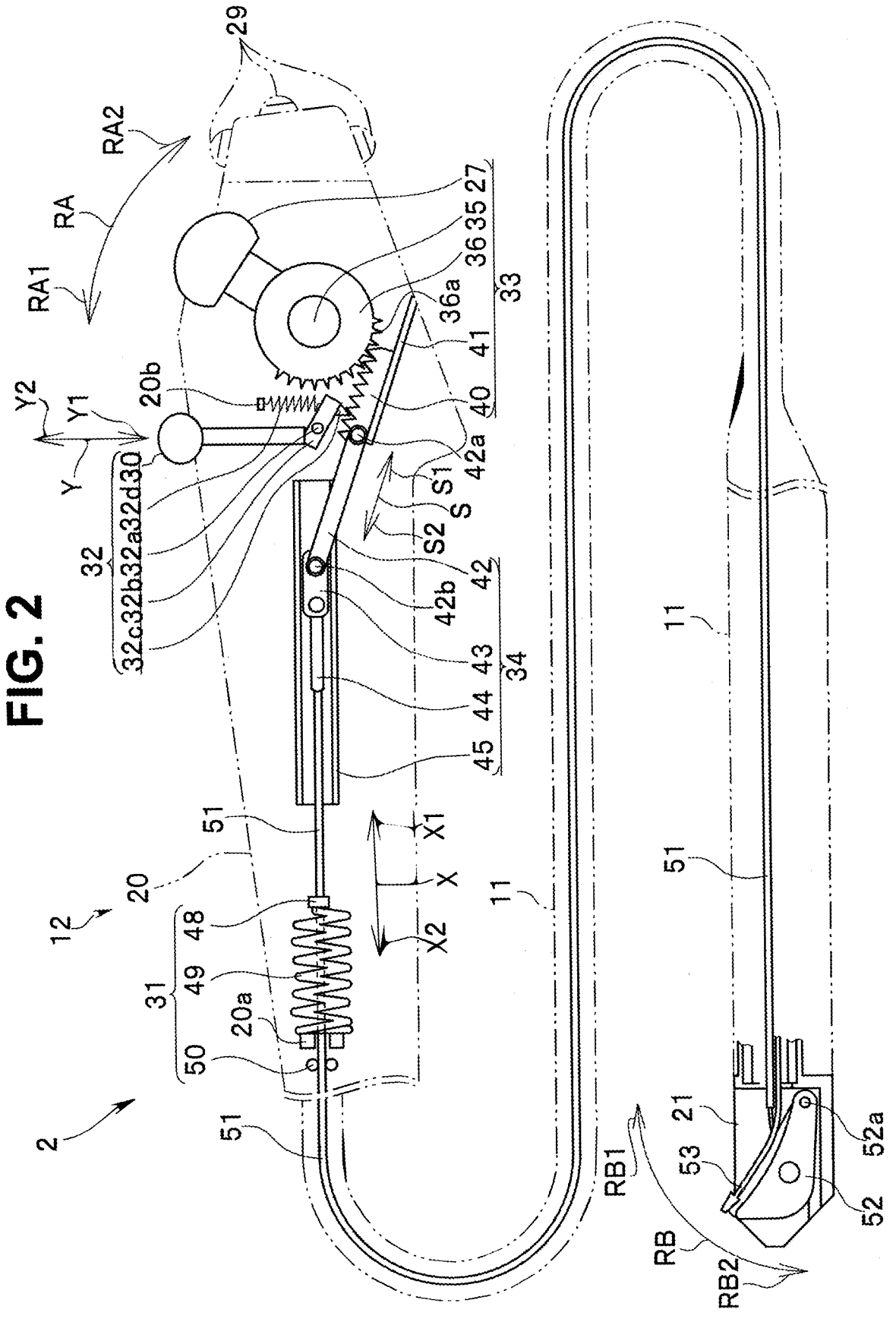
FIG. 2 is a schematic configuration diagram mainly illustrating a raising base and a raising-base-related mechanism unit in the endoscope in FIG. 1 (a first state of a switching mechanism).

As illustrated in FIG. 2 and as described above, the raising base 52 is included in the distal end portion 21 of the insertion portion 11. The raising base 52 is rotatably supported by a support shaft 52a. The support shaft 52a is a shaft member fixed to a fixed part of the distal end portion 21. The support shaft 52a is disposed in a direction orthogonal to a long-axis direction of the insertion portion 11. With this configuration, the raising base 52 performs forward and reverse rotation about the support shaft 52a.

Note that an internal structure of the distal end portion 21 including the raising base 52 and a configuration of the raising base 52 are the same as a configuration of a conventional endoscope of the same kind. Thus, detailed description of the configurations of the distal end portion 21 and the raising base 52 is omitted in description of the present embodiment.

A distal end of the pulling wire 51 is connected to the raising base 52. The pulling wire 51 extends from the raising base 52 to inside of the operation portion 12 through inside of the insertion portion 11. In other words, the pulling wire 51 is an elongated member connected to the raising base 52 and extended to the operation portion 12. A proximal end of the pulling wire 51 is connected to a predetermined site (to be described later in details; refer to reference sign 44 in FIG. 2) of a raising-base-related mechanism unit. In this case, the pulling wire 51 is disposed inside the insertion portion 11 in a state in which the pulling wire 51 is freely movable forward and backward in the long-axis direction of the insertion portion 11. Note that a predetermined region (at least a part corresponding to a wire coupling member 44 to be described later and the biasing force generation mechanism 31) on the proximal end side of the pulling wire 51 is formed to be stronger against buckling, in particular, or stronger against external force in a direction intersecting a long-axis direction (direction along an arrow X to be described later) than the other part. Alternatively, the region of the pulling wire 51 may be formed of a material different from a material of the other part. In this case, the region of the pulling wire 51 is formed of a material that is more unlikely to buckle than the other part or a material that is strong against external force in a direction intersecting the long-axis X direction.

Note that the pulling wire 51 receives predetermined drive power (biasing force or operational force) to be described later and moves in a direction illustrated with the arrow X in FIG. 2. In this case, a direction illustrated with an arrow X1 in FIG. 2 is referred to as a pulling direction of the pulling wire 51. The raising base 52 is raised as the pulling wire 51 moves in the pulling direction X1. A direction illustrated with an arrow X2 in FIG. 2 is referred to as an extrusion direction of the pulling wire 51. The raising base 52 is laid down as the pulling wire 51 moves in the extrusion direction X2.

With such a configuration, the pulling wire 51 moves forward and backward in the direction along the arrow X between the operation portion 12 and the raising base 52. Accordingly, the raising base 52 performs forward and reverse rotation about the support shaft 52a. Accordingly, the raising base 52 is driven to be raised or laid down. Thus, the pulling wire 51 functions as a transmission member that transmits drive power for raising or laying down the raising base 52. Note that the raising base 52 receives the above-described drive power and moves in a direction illustrated with an arrow RB in FIG. 2. In this case, a direction illustrated with an arrow RB1 in FIG. 2 is a direction in which the raising base 52 is raised. A direction illustrated with an arrow RB2 in FIG. 2 is a direction in which the raising base 52 is laid down.

The biasing force generation mechanism 31, the switching mechanism 32, the raising-base lay-down operation mechanism 33, and the drive power transmission mechanism 34 are provided as raising-base-related mechanism units inside the operation portion 12.

The biasing force generation mechanism 31 is a mechanism unit for constantly applying biasing force in a predetermined direction to the pulling wire 51. The predetermined direction is a direction for constantly keeping the raising base 52 in a raised state.

The biasing force generation mechanism 31 includes a biasing force generation member 49 and a speed reduction member 50. The biasing force generation member 49 can be called a biasing element. The biasing force generation member 49 is attached to the pulling wire 51 and configured to apply to the pulling wire 51 the biasing force in a raising direction RB1. One end of the biasing force generation member 49 is supported to an internal fixed part 20*a* of the operation portion 12. The other end of the biasing force generation member 49 is fixed to a fastener 48 fixed to a predetermined site of the pulling wire 51. With this configuration, the biasing force generation member 49 constantly applies, to the pulling wire 51, biasing force that drives the raising base 52 in the raising direction RB1. The pulling wire 51 is configured to move in the raising direction RB1 to raise the raising base. In this case, a moving amount of the pulling wire 51 when moved by the biasing force by the biasing force generation mechanism 31 is restricted to a predetermined range. For example, when the pulling wire 51 moves as the biasing force generation member 49 extends, the fastener 48 eventually contacts an end part of a wire guide 45 to be described later. Accordingly, movement of the pulling wire 51 is restricted to the predetermined range. Note that the biasing force generation member 49 may be, for example, an extension-contraction coil spring as illustrated in FIG. 2 or a pneumatic or hydraulic damper device. Moreover, a configuration that restricts movement of the pulling wire 51 is not limited to the above-described configuration in which the fastener 48 contacts the end part of the wire guide 45, but may be any other configuration. For example, a stopper member configured to restrict a raised amount of the raising base 52 may be provided inside the distal end portion 21. With such a configuration, it is possible to restrict the moving amount of the pulling wire 51 by restricting the raised amount of the raising base 52. The biasing force generation member 49 has a first end connected to the internal fixed part 20*a* of the operation portion and a second end connected to the pulling wire 51.

The speed reduction member 50 is a member configured to reduce a speed at which the raising base 52 is driven in the raising direction RB1 by the biasing force by the biasing force generation member 49. The speed reduction member 50 includes at least a frictional member configured to apply frictional force to movement of a pulling wire. Specifically, the speed reduction member 50 is, for example, a rubber ring, a damper, or a friction block. The speed reduction member 50 according to the present embodiment includes an O-shaped ring that holds inside an outer peripheral surface of the pulling wire 51 with a predetermined amount of force. The speed reduction member 50 is configured to reduce a speed at which the raising base 52 is raised by the biasing force of the biasing force generation member 49. The speed reduction member 50 includes a frictional member configured to apply a frictional force to the pulling wire 51. A first end of the biasing member third is fixed to the switching mechanism 32 and a second end of the biasing member third is fixed to an internal surface of the operation portion 12.

The switching mechanism 32 includes the switching operation member 30, a support shaft 32*a*, a lever 32*b*, a lock click 32*c*, and a spring 32*d*.

The switching operation member 30 is an operation member that receives operational force by a finger of an endoscope operator (not illustrated) or the like, acts on the switching mechanism 32, and switches the state of the raising base 52.

A distal end of the switching operation member 30 acts on one end of the lever 32*b*. The other end of the switching operation member 30 is disposed at a position exposed outside the operation portion 12. The endoscope operator (not illustrated) applies operational force on the switching operation member 30 by placing a finger on the other end part of the switching operation member 30. The switching operation member 30 is provided to be freely movable in a direction along an arrow Y in FIG. 2. Accordingly, the switching operation member 30 receives pressing operational force in an arrow Y1 direction in FIG. 2 and acts on the one end of the lever 32*b*. Note that the arrow Y direction and the arrow Y1 direction are directions along a long axis of the switching operation member 30. Similarly, an arrow Y2 direction to be described later is a direction along the long axis of the switching operation member 30.

The lever 32*b* is a plate-shaped or bar-shaped member provided to be rotatable in a predetermined range about the support shaft 32*a*. The support shaft 32*a* is a shaft member fixed to an internal fixation member of the operation portion 12. One end of the extendable spring 32*d* is fixed to the other end of the lever 32*b*. The other end of the spring 32*d* is fixed to an internal fixed part 20*b* of the operation portion 12.

With this configuration, biasing force by the spring 32*d* in an extension direction constantly presses the other end of the lever 32*b*. Accordingly, the lever 32*b* receives the biasing force by the spring 32*d* and is rotationally urged in a clockwise direction with the support shaft 32*a* as a rotation center in FIG. 2. With the rotational biasing force on the lever 32*b*, the one end of the lever 32*b* contacts the distal end of the switching operation member 30. In this case, the one end of the lever 32*b* applies, to the switching operation member 30, an amount of force for movement in the arrow Y2 direction in FIG. 2. The switching mechanism 32 includes a biasing member 32*d* and a locking member 32*c*, and the biasing member 32*d* applies a biasing force to the switching mechanism 32 to bias an engagement between the locking member 32*c* and an engagement member 40.

In this case, rotation of the lever 32*b* is restricted to a predetermined range. With this configuration, movement of the switching operation member 30 in the arrow Y2 direction is restricted to a predetermined range, as well. Accordingly, the switching operation member 30 is held at a predetermined position inside the operation portion 12.

With such a configuration, the support shaft 32*a* functions as a pivot of the lever 32*b*, the one end of the lever 32*b* functions as a point of effort, the other end of the lever 32*b* functions as a point of action, and the lever 32*b* functions as a lever.

Note that the lock click 32*c* is formed on one surface of the other end of the lever 32*b*. The lock click 32*c* locks to a gear train of a rack 40 of the raising-base lay-down operation mechanism 33 to be described later when the other end of the lever 32*b* receives extension biasing force by the spring 32*d* and rotates the lever 32*b* in the clockwise direction in FIG. 2. With this configuration, rotation of the lever 32*b* is restricted. The rack 40 can be connected directly or indirectly to the pulling wire 51.

When pressing operational force in the arrow Y1 direction is applied to the switching operation member 30, the distal end of the switching operation member 30 presses the one end of the lever 32*b*. The lever 32*b* receiving the pressing operational force rotates in an anticlockwise direction in FIG. 2 against the biasing force by the spring 32*d*. With this configuration, engagement between the lock click 32c and the gear train of the rack 40 is released.

In this manner, the switching mechanism 32 is a mechanism unit having a function to switch between a state in which the lock click 32c and the gear train of the rack 40 are engaged with each other and a state in which engagement between the lock click 32c and the gear train of the rack 40 is released.

The raising-base lay-down operation mechanism 33 is a mechanism unit for causing transition of the raising base 52 from the raised state to a laid-down state as a predetermined operation (operation to lay down the raising base 52) is performed against the biasing force by the biasing force generation mechanism 31 in the predetermined direction (direction in which the raising base 52 is raised).

The raising-base lay-down operation mechanism 33 includes the raising operation lever 27, a main support shaft 35, a rotation member 36, the rack 40, and a rack guide 41.

The raising operation lever 27 is a second operation member that receives operational force by a finger of the endoscope operator (not illustrated) or the like, acts on the raising-base lay-down operation mechanism 33, and causes transition of the raising base 52 from the raised state to the laid-down state. In this case, the raising operation lever 27 receives the operational force and rotates the rotation member 36. Thus, the raising operation lever 27 is formed integrally with the rotation member 36. The raising operation lever 27 is freely rotatable in a predetermined range in a direction illustrated with an arrow RA in FIG. 2. In this case, a direction illustrated with an arrow RA1 in FIG. 2 is the direction in which the raising base 52 is raised. A direction illustrated with an arrow RA2 in FIG. 2 is the direction in which the raising base 52 is laid down. Note that the operation lever 27 may be combined with any other component as long as the operation lever 27 is formed integrally with the rotation member 36, and the operation lever 27 may be combined with a non-illustrated link mechanism or the like to allow adjustment of the amount of operational force. The raising base operator 27 includes the rotation member 36 being configured to rotate about a shaft 35, and the coupling unit 33 includes an engagement member 40. Engagement of the raising base operator 27 with the coupling unit 33 includes engagement by a surface of the rotation member with the engagement member 40, and movement of the raising base operator 27 between the first position and the second position includes rotation of the rotation member 36. The surface of the rotation member 36a includes a first plurality of teeth and defines a pinion, the engagement member 40 includes a plurality of teeth and defines a rack, and the pinion and the rack cooperate in a rack and pinion structure.

The rotation member 36 is a circular disk member configured to rotate about the main support shaft 35. The rotation member 36 is provided with a gear 36a in at least a predetermined region of an outer periphery portion. The main support shaft 35 is a shaft member fixed to the internal fixation member of the operation portion 12. The main support shaft 35 is disposed with an axial direction in a direction substantially orthogonal to a moving direction X of the pulling wire 51.

The rack 40 is an engagement member provided with a plate-shaped gear train that is engaged with the gear 36a of the rotation member 36. With this configuration, the rack 40 linearly moves in a predetermined direction in accordance with rotation of the rotation member 36. The rack 40 is coupled to the pulling wire 51 through the drive power transmission mechanism 34 to be described later. Accordingly, the pulling wire 51 moves in a direction along the moving direction X as the rack 40 linearly moves.

Note that installation is made such that the gear 36a of the rotation member 36 contacts the gear train of the rack 40 in a substantially perpendicular direction when the gear 36a of the rotation member 36 is engaged with the gear train of the rack 40.

The rack guide 41 is a support member configured to guide linear movement of the rack 40. The rack guide 41 is formed of a flat plate member or the like. The rack guide 41 is disposed in parallel to a direction along an arrow S illustrated in FIG. 2. The rack 40 slides on one plane of the rack guide 41. With this configuration, the rack guide 41 guides movement of the rack 40 in a predetermined direction. Accordingly, the rack 40 moves in the direction along the arrow S.

The drive power transmission mechanism 34 is a mechanism unit that couples the biasing force generation mechanism 31 and the raising-base lay-down operation mechanism 33.

The drive power transmission mechanism 34 includes a first link member 42, a first link shaft 42a, a second link shaft 42b, a second link member 43, the wire coupling member 44, and the wire guide 45.

One end of the first link member 42 is connected to the rack 40 by the first link shaft 42a. The other end of the first link member 42 is connected to one end of the second link member 43 by the second link shaft 42b. One end of the wire coupling member 44 is connected to the other end of the second link member 43. The proximal end of the pulling wire 51 is connected to the other end of the wire coupling member 44.

The second link member 43 is disposed to be freely linearly movable inside a groove of the wire guide 45 in the direction along the arrow X in FIG. 2. The wire guide 45 is disposed in parallel to the moving direction X of the pulling wire 51. The first link member 42 is disposed at a predetermined angle relative to the wire guide 45. In the state illustrated in FIG. 2 (the laid-down state of the raising base 52), the first link member 42 is disposed in parallel to the direction along the arrow S.

With such a configuration, for example, when the pulling wire 51 receives the biasing force by the biasing force generation mechanism 31 and moves in the arrow X1 direction, the wire coupling member 44, the second link member 43, and the second link shaft 42b move in the same arrow X1 direction along the groove of the wire guide 45. In this case, the other end of the first link member 42 moves in the arrow X1 direction together with the second link shaft 42b.

The one end of the first link member 42 moves in an arrow 51 direction together with the first link shaft 42a. Accordingly, the rack 40 moves in the same arrow 51 direction. Then, transition is made to a state illustrated in FIG. 3. The state illustrated in FIG. 3 indicates the raised state of the raising base 52.

Note that, as described above, the switching mechanism 32 has a function to switch between the state in which the lock click 32c and the gear train of the rack 40 are engaged with each other and the state in which engagement between the lock click 32c and the gear train of the rack 40 is released.

The state in which the lock click 32c and the gear train of the rack 40 are engaged with each other is a state in which the biasing force by the biasing force generation mechanism 31 is restrained to stop movement of the pulling wire 51 and raising operation of the raising base 52 as illustrated in FIG.

2. This state is referred to as a first state. Note that the state illustrated in FIG. 2 indicates a state in which the raising base 52 is laid down most. In this state, the biasing force by the biasing force generation mechanism 31 is stored most.

The state in which engagement between the lock click 32*c* and the gear train of the rack 40 is released is a state in which the biasing force by the biasing force generation mechanism 31 is released to allow free movement of the pulling wire 51 in a predetermined direction (the arrow X1 direction) and raising operation of the raising base 52. This state is referred to as a second state. Note that the state illustrated in FIG. 3 indicates a state in which the raising base 52 is raised most. In this state, the biasing force by the biasing force generation mechanism 31 is released most.

In other words, the switching mechanism 32 has a function to switch between the first state and the second state.

The switching mechanism 32 according to the present embodiment is configured as a dog clutch (engaging clutch) configured to switch between the first state in which engagement is made with the gear train of the rack 40 and the second state in which the engagement is released. In this case, the dog clutch is engaged with the rack 40 in the first state, thereby suppressing the biasing force by the biasing force generation mechanism 31 and controlling operation of the pulling wire 51. The switching mechanism 32 includes a clutch movable between an engaged state and a non-engaged state, and in the engaged state, the clutch engages with the pinion or the rack 40 and, in the non-engaged state, the clutch is not engaged with the pinion or the rack 40. The switching mechanism is in the first state, the clutch is in the engaged state. The switching mechanism includes a rack connected to the wire, and a clutch configured to switch between an engaged state and a non-engaged state. In the engaged state, the clutch engages with the rack and, in the non-engaged state, the clutch is not engaged with the rack.

Note that, in addition to the above-described configuration, the switching mechanism 32 may include, for example, a clutch mechanism configured to raise the raising base 52 at stages as operations are performed a plurality of times.

Effects of the endoscope 2 according to the present embodiment thus configured when the raising base 52 is used will be described below with reference to FIGS. 2 and 3.

In the endoscope 2 according to the present embodiment, the pulling wire 51 for operating the raising base 52 is constantly urged with biasing force by the biasing force generation member 49 of the biasing force generation mechanism 31 in the direction in which the raising base 52 is raised.

Thus, the state of the raising base 52 of the endoscope 2 is first set in the state illustrated in FIG. 2 before the endoscope 2 is used. The state illustrated in FIG. 2 is the state in which the raising base 52 is laid down. In this state, the switching mechanism 32 is in the first state in which the lock click 32*c* and the gear train of the rack 40 are engaged with each other. In this case, the biasing force by the biasing force generation mechanism 31 is suppressed in a state of being stored. Accordingly, in this case, movement of the pulling wire 51 and raising operation of the raising base 52 are stopped.

In this state, the endoscope operator performs a normal endoscope operation to insert the insertion portion 11 into a body cavity of a subject. Then, when the distal end portion 21 of the insertion portion 11 has reached near a target site at which a procedure is to be performed, the endoscope operator performs a normal endoscope operation to introduce the treatment instrument 53 through the forceps port 25 of the operation portion 12 and dispose a distal end of the treatment instrument 53 near the distal end portion 21.

In this state, the switching operation member 30 is operated by pressing in the arrow Y1 direction in FIG. 2. Upon the pressing operation, the switching mechanism 32 switches to the second state in which engagement between the lock click 32*c* and the gear train of the rack 40 is released.

When engagement between the lock click 32*c* and the gear train of the rack 40 is released in this manner, the stored biasing force by the biasing force generation mechanism 31 is released. Accordingly, the pulling wire 51 receives the biasing force by the biasing force generation mechanism 31 and moves in the arrow X1 direction in FIG. 2. As the pulling wire 51 moves in the arrow X1 direction, the raising base 52 rotates in a predetermined range in the arrow RB1 direction in FIG. 2. Accordingly, the raising base 52 is raised. In this case, a moving speed of the pulling wire 51 is reduced by an effect of the speed reduction member 50. Accordingly, the raising base 52 is not abruptly raised.

In this case, simultaneously with the raising operation of the raising base 52, the pulling wire 51 acts on the raising-base lay-down operation mechanism 33 through the drive power transmission mechanism 34 and moves the rack 40 in the arrow 51 direction in FIG. 2. Accordingly, the rack 40 rotates the rotation member 36 about the main support shaft 35 in the anticlockwise direction in FIG. 2. As a result, the raising operation lever 27 inclines in the arrow RA1 direction from a position illustrated in FIG. 2 to a position illustrated in FIG. 3. Accordingly, the endoscope 2 transitions to the state illustrated in FIG. 3. In this manner, it is possible to change the leading direction of the treatment instrument 53 by raising the raising base 52. When the pressing operation on the switching operation member 30 in the arrow Y1 direction is released, the switching mechanism 32 switches to the first state in which the lock click 32*c* and the gear train of the rack 40 are engaged with each other. Accordingly, the raised state of the raising base 52 is maintained.

Then, treatment is performed by using the treatment instrument 53. During an operation of the treatment, since the raised state of the raising base 52 is maintained, the endoscope operator does not need to perform an operation related to the raising operation and can focus on any other bending operation and treatment instrument operation.

Subsequently, when the raised state of the raising base 52 has become unnecessary since a procedure or the like ends, an operation to cause transition from the state illustrated in FIG. 3 to the state illustrated in FIG. 2 by laying down the raising base 52 is performed. Note that, before this operation is performed, for example, an operation to remove the treatment instrument 53 is performed.

Figure 3:
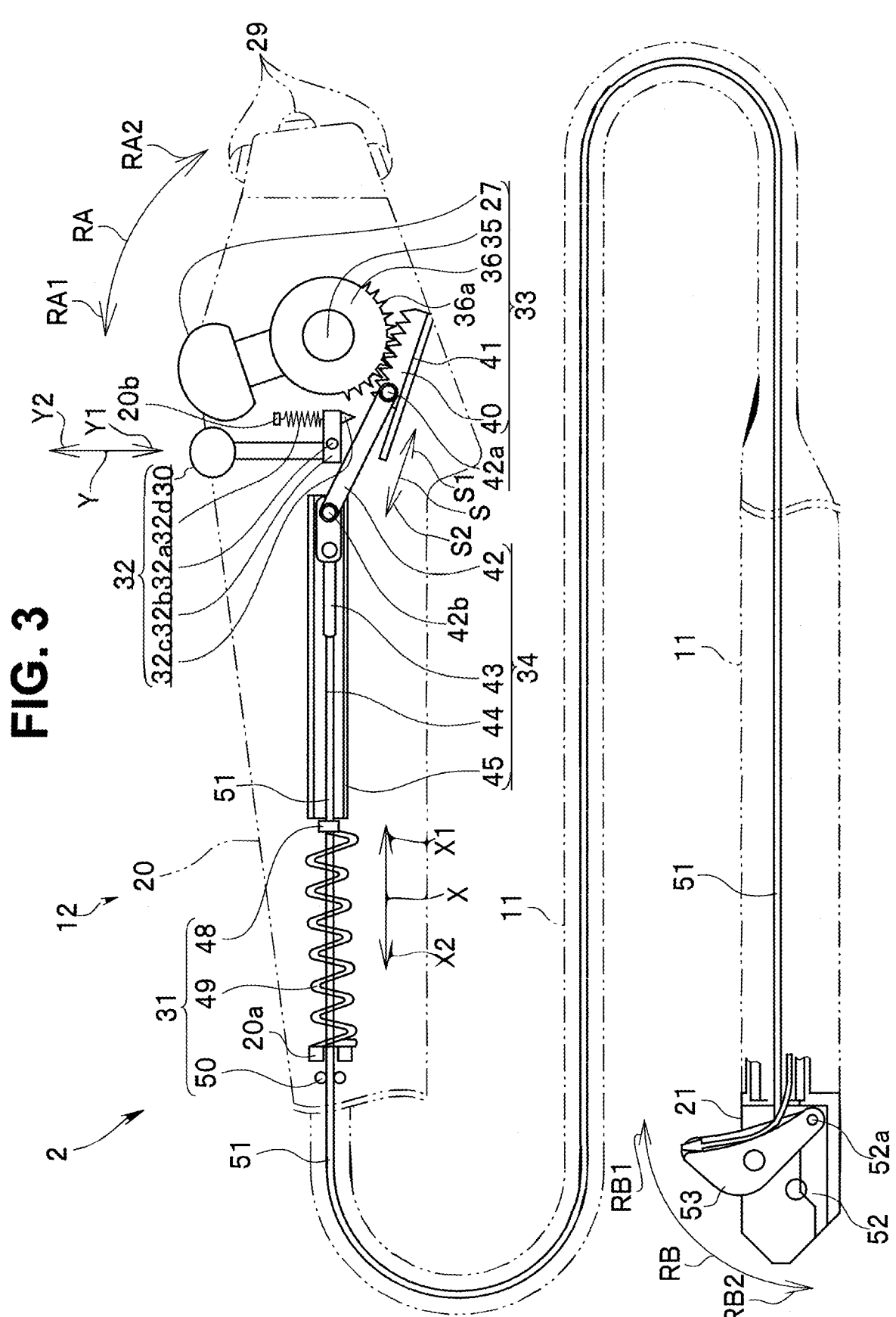
FIG. 3 is a schematic configuration diagram illustrating a status after the switching mechanism transitions from the first state to a second state, indicating an effect of the endoscope in FIG. 1.

In FIG. 3, the raising operation lever 27 is first inclined in an arrow RA2 direction from the position illustrated in FIG. 3 to the position illustrated in FIG. 2 while pressing operation on the switching operation member 30 in the arrow Y1 direction is maintained. Accordingly, the rotation member 36 rotates about the main support shaft 35 in a clockwise direction in FIG. 3. As a result, the rotation member 36 moves the rack 40 in an arrow S2 direction in FIG. 3.

Accordingly, the raising-base lay-down operation mechanism 33 acts on the pulling wire 51 through the drive power transmission mechanism 34. In this case, the pulling wire 51 moves in the arrow X2 direction against the biasing force by the biasing force generation mechanism 31. Along with the movement of the pulling wire 51 in the arrow X2 direction, the biasing force generation member 49 of the biasing force generation mechanism 31 is contracted. Then, in this case, the raising base 52 rotates in a predetermined range in the arrow RB2 direction in FIG. 3. Accordingly, the raising base 52 is laid down and transitions to the state illustrated in FIG. 2. Note that the transition to the laid-down state can be checked based on incapability of performing an operation on the raising operation lever 27.

After the raising base 52 has transitioned to the state illustrated in FIG. 2, the pressing operation on the switching operation member 30 is released. As a result, the biasing force by the spring 32*d* acts on the lever 32*b*, and the switching operation member 30 moves in the arrow Y2 direction and returns to the state illustrated in FIG. 2. Accordingly, the switching mechanism 32 returns to the first state in which the lock click 32*c* and the gear train of the rack 40 are engaged with each other.

Note that, when the raising base 52 moves from the state in FIG. 2 to the state in FIG. 3, the pressing operation on the switching operation member 30 may be released at any timing. In this case, the raised state of the raising base 52 can be set to a position.

The raised state of the raising base 52 can be changed after the raising base 52 has become the raised state in FIG. 3. In this case, the above-described operation to cause transition of the raising base 52 to the laid-down state is performed, and the pressing operation on the switching operation member 30 is released when the raising base 52 has become a raised state (halfway position between the raised state in FIG. 3 and the laid-down state in FIG. 2).

In this manner, the raised state of the raising base 52 can be maintained at a halfway position between the raised state in FIG. 3 and the laid-down state in FIG. 2.

As described above, the embodiment includes the biasing force generation mechanism 31 configured to constantly apply, to the pulling wire 51, biasing force in a direction of raising operation of the raising base 52; the switching mechanism 32 configured to switch between the first state and the second state, the first state being a state in which the biasing force by the biasing force generation mechanism 31 is restrained to stop raising operation of the raising base 52, the second state being a state in which the biasing force by the biasing force generation mechanism 31 is released to allow raising operation of the raising base 52; and the switching operation member 30 configured to act on the switching mechanism 32 to cause switching between the first state and the second state upon receiving operational force.

With this configuration, in the endoscope 2 according to the present embodiment, when the raising base 52 is to be raised, it is possible to cause transition of the raising base 52 to the raised state by performing a pressing operation on the switching operation member 30. The raised state of the raising base 52 is maintained by the biasing force by the biasing force generation mechanism 31 without no operation for maintaining the raised state.

In this case, the speed reduction member 50 configured to reduce a speed at which the raising base 52 is raised by the biasing force by the biasing force generation mechanism 31 is further provided. The speed reduction member 50 prevents the raising base 52 from being abruptly raised. Thus, a secure raising operation can be constantly performed.

Accordingly, for example, when the endoscope operator performs a raising operation of the raising base 52 simultaneously with an operation on the bending operation member 26 of the endoscope 2, it is possible to reduce a load on fingers of the endoscope operator and improve operability of the endoscope 2 since an operation for the raising operation of the raising base 52 is simplified. Moreover, the endoscope operator can focus on an endoscope operation other than the raising operation, for example, a procedure-related operation such as a treatment instrument positioning operation.

The present embodiment further includes the raising-base lay-down operation mechanism 33 configured to cause transition of the raising base 52 from the raised state to the laid-down state when operated against the biasing force by the biasing force generation mechanism 31; and the raising operation lever 27 configured to act on the raising-base lay-down operation mechanism 33 to cause transition of the raising base 52 from the raised state to the laid-down state upon receiving operational force.

With this configuration, in the endoscope 2 according to the present embodiment, for example, when the raising base 52 is to be laid down after a procedure, it is possible to return the raising base 52 to the laid-down state by performing an operation to incline the raising operation lever 27 in a predetermined direction while maintaining a pressing operation on the switching operation member 30.

In this case, the raising-base lay-down operation mechanism 33 includes the rotation member 36 configured to rotate about the main support shaft 35 and provided with the gear 36*a* on the outer periphery portion, and the rack 40 provided with the gear train that is engaged with the gear 36*a* of the rotation member 36. In this case, the rack 40 is coupled to the pulling wire 51. The rack 40 moves forward and backward in accordance with rotation of the rotation member 36. The raising operation lever 27 is configured to rotate the rotation member 36 upon receiving operational force.

The gear 36*a* of the rotation member 36 is installed such that the gear 36*a* of the rotation member 36 contacts the gear train of the rack 40 in a substantially perpendicular direction. With this configuration, a constant amount of force can be applied to the gear train of the rack 40 irrespective of an inclined position of the raising operation lever 27 as long as a constant amount of force is applied to the raising operation lever 27.

With this configuration, the raising operation lever 27 rotates the rotation member 36. The rotation member 36 moves the rack 40 forward and backward. In other words, the rotation member 36 converts rotation motion into linear motion. The rack 40 moves the pulling wire 51 in the long-axis direction.

With such a configuration, in the endoscope 2 according to the present embodiment, a necessary amount of operational force does not change depending on the inclined position of the raising operation lever 27. Accordingly, it is possible to reduce a load on the endoscope operator and improve operability.

Note that, in the above-described embodiment, the switching mechanism 32 restrains the biasing force by the biasing force generation mechanism 31 by engaging the lock click 32*c* with the gear train of the rack 40. However, the switching mechanism 32 is not limited to such an exemplary configuration.

For example, rotation of the rotation member 36 may be prevented by engaging the lock click 32*c* with the gear 36*a* of the rotation member 36. Even with a configuration that prevents rotation of the rotation member 36, the gear 36*a* of the rotation member 36 is constantly engaged with the gear train of the rack 40, and thus can be switched between the first state and the second state by the switching mechanism 32.

In the above-described embodiment, the raising-base lay-down operation mechanism 33 exemplarily has a configuration in which the gear 36*a* of the rotation member 36 is directly engaged with the gear train of the rack 40. However, the raising-base lay-down operation mechanism 33 is not limited to the exemplary configuration.

For example, another gear may be interposed between the gear 36*a* of the rotation member 36 and the gear train of the rack 40. In this case, one or a plurality of gears may be interposed. When such a configuration is employed, for example, it is possible to change an operation direction of the raising operation lever 27. In addition, it is possible to achieve deceleration by adjusting the number of interposed gears and the number of teeth. In this case, it is possible to reduce the amount of operational force when the raising operation lever 27 is operated against the biasing force by the biasing force generation mechanism 31.

In the above-described embodiment, an amount of force in a direction (the arrow Y2 direction in FIG. 2) in which the switching operation member 30 is pressed upward is constantly applied to the lever 32*b* of the switching mechanism 32 by biasing force in the extension direction of the spring 32*d*. Accordingly, the switching operation member 30 moves in the arrow Y1 direction when pressing operational force is applied, and moves in the arrow Y2 direction when pressing operational force is released. With this configuration, a pressing operation on the switching operation member 30 needs to be continuously maintained to maintain a state in which engagement between the lock click 32*c* and the gear train of the rack 40 is released.

Thus, for example, an operation member of a push-lock type may be employed to maintain a pressing operation on the switching operation member 30 in the arrow Y1 direction. When such an operation member of the push-lock type is employed, it is possible to maintain the second state of the switching mechanism 32 by performing a pressing operation on the switching operation member 30 once. Accordingly, it is possible to further reduce a load on the endoscope operator and further improve operability.

In the above-described embodiment, the switching mechanism 32 has a structure in which forward and backward movement of the rack 40 is completely prevented when the lock click 32*c* is engaged with the gear train of the rack 40. However, the switching mechanism 32 is not limited to the exemplary structure.

For example, the engagement structure of the lock click 32*c* and the gear train of the rack 40 may be such that movement of the rack 40 in the arrow 51 direction is completely prevented but movement of the rack 40 in the arrow S2 direction is allowed when the lock click 32*c* and the gear train of the rack 40 are engaged with each other. Such a structure can be achieved by contriving the shape of the lock click 32*c* and the shape of the gear train of the rack 40. Specifically, for example, a structure employed for a typical well-known banding band or the like in practical use is applicable. Specifically, for example, in at least one of teeth and a rack meshed with each other as a dog clutch, one surface of teeth on a side on which a meshed state may be maintained is formed in a substantially perpendicular shape. Teeth on a side on which motion similar to an idle running state can be at a lever operation are formed at an angle smaller than 90°. With such a configuration, a structure that prevents movement in one direction but allows movement in the other direction can be achieved. The switching mechanism 32 includes a detent 32*c* connected to a lever 30, and in the first state, the detent 32*c* is engaged with the coupling unit 40 and, in the second state, the detent 32*c* is disengaged from the coupling unit 40.

With such a configuration, when the raising base 52 is to be returned from the raised state illustrated in FIG. 3 to the laid-down state illustrated in FIG. 2, a pressing operation on the switching operation member 30 does not need to be performed but the raising operation lever 27 needs to be operated in the arrow RA2 direction. Accordingly, it is possible to further improve operability.

In the above-described embodiment, the raising-base lay-down operation mechanism 33 has a configuration in which the gear 36*a* of the rotation member 36 is engaged with the gear train of the rack 40 and the rotation member 36 is rotated by manually operating the raising operation lever 27. However, the raising-base lay-down operation mechanism 33 is not limited to the exemplary configuration.

For example, the raising-base lay-down operation mechanism 33 may be configured by using an actuator capable of outputting an amount of force that rotates the rotation member 36 (moves the rack 40) against the biasing force by the biasing force generation mechanism 31 or by using a hydraulic or pneumatic damper device or the like.

In the above-described embodiment, the biasing force generation mechanism 31 has a configuration in which the biasing force generation member 49 is provided at a middle part (inside the operation portion 12) of the pulling wire 51 connected to the raising base 52. However, the biasing force generation mechanism 31 is not limited to the exemplary configuration.

For example, a torsion coil spring or the like may be disposed about the support shaft 52*a* of the raising base 52 to apply biasing force in the raising direction to the raising base 52. With this configuration, a rotation restricting member is provided such that rotation of the raising base 52 is restricted in a predetermined range.

In the above-described embodiment, the speed reduction member 50 sandwiches the outer peripheral surface of the pulling wire 51 with a predetermined amount of force. However, the speed reduction member 50 is not limited to the exemplary configuration.

For example, an adjustment dial or the like may be provided near the bend preventing portion 24 of the operation portion 12 so that the internal fixed part 20*a* supporting the one end of the biasing force generation member 49 can be moved in the long-axis direction (the moving direction of the pulling wire 51) through an operation on the adjustment dial.

With this configuration, it is possible to perform adjustment such as reduction of the biasing force by the biasing force generation member 49 by adjusting a position of the internal fixed part 20*a* in accordance with an operation on the adjustment dial. When the biasing force by the biasing force generation member 49 can be adjusted, the speed and amount of force at which the raising base 52 is raised can be adjusted. Moreover, for example, when a problem has occurred to a raising or lay-down operation of the raising base 52, the raising base 52 can securely transition to the laid-down state without being prevented by the biasing force by the biasing force generation member 49.

In the above-described embodiment, the switching mechanism 32 switches between the first state and the second state upon a pressing operation on the switching operation member 30 in the long-axis direction (the arrow Y1 direction). However, the switching mechanism 32 is not limited to the exemplary configuration.

Figure 4:
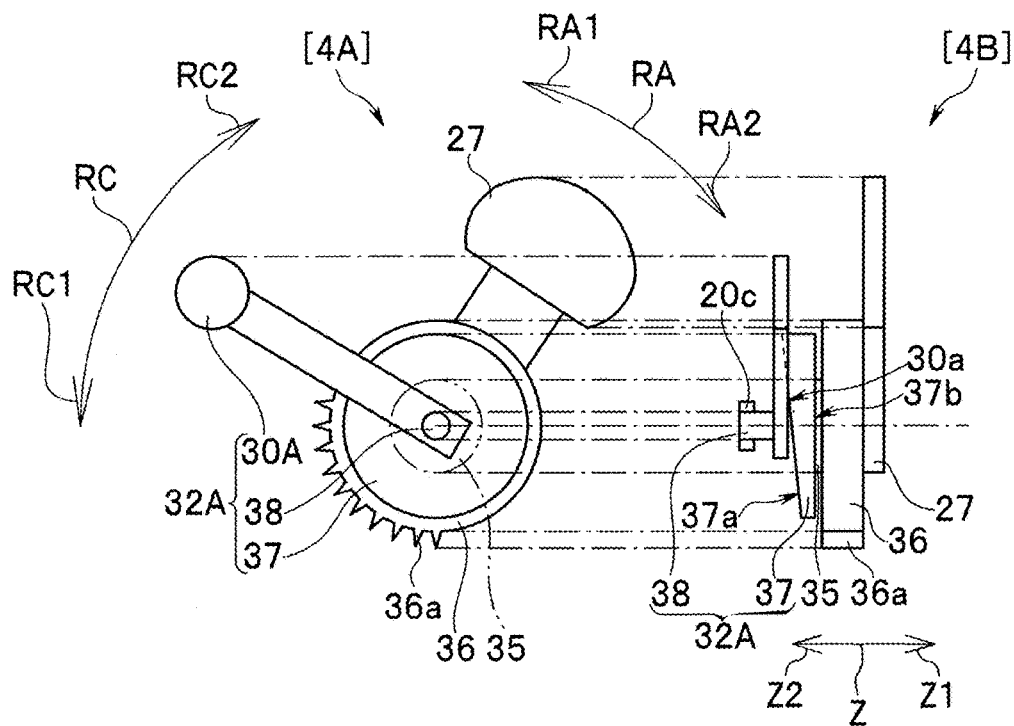
FIG. 4 is a diagram illustrating a configuration of a modification of the switching mechanism in the endoscope according to the embodiment of the present disclosure.

For example, FIG. 4 is a diagram illustrating a configuration of a modification of the switching mechanism in the endoscope of the above-described embodiment. Note that, in 17 18

FIG. 4, reference sign [4A] denotes a plan view. In FIG. 4, reference sign [4B] denotes a side view.

As illustrated in FIG. 4, a switching mechanism 32A includes a switching operation member 30A, a pressing plate 37, and an auxiliary support shaft 38.

The switching operation member 30A is disposed to be able to perform forward and reverse rotation in a predetermined direction (arrow RC direction in FIG. 4) in a predetermined range about the auxiliary support shaft 38 having one end pivotally supported to an internal fixed part 20c of the operation portion 12.

The pressing plate 37 is a pressing member formed of a thin plate member that has a tilt surface 37a provided with a ridged-shape protrusion portion formed on one surface and has a disk shape as a whole. The pressing plate 37 is integrally pivotally supported to the rotation member 36 through the main support shaft 35 in a rotational direction and provided to be freely movable in a predetermined range in a direction along an arrow Z in FIG. 4 in an axial direction. The tilt surface 37a of the pressing plate 37 faces a shaft-portion side surface 30a of the switching operation member 30A. A surface 37b of the pressing plate 37 on a side opposite to the tilt surface 37a faces one surface (outer surface) of the rotation member 36. The opposite surface 37b of the pressing plate 37 is substantially in parallel to the one surface of the rotation member 36.

Note that configurations of the rotation member 36 and the raising operation lever 27 are the same as in the above-described embodiment.

With such a configuration, in the switching mechanism 32A, when the switching operation member 30 is inclined about the support shaft 38 in the direction illustrated with the arrow RC in FIG. 4, the pressing plate 37 moves in an arrow Z1 direction and is pressed against a plane of the rotation member 36 or the pressing plate 37 moves in an arrow Z2 direction and is separated from the plane of the rotation member 36.

For example, in FIG. 4, when the switching operation member 30A is rotated about the support shaft 38 in, for example, an arrow RC1 direction (anticlockwise direction; first direction), the pressing plate 37 moves in the arrow Z1 direction and is pressed against the plane of the rotation member 36. Rotation of the rotation member 36 is prevented when the pressing plate 37 is pressed against the rotation member 36. Accordingly, forward and backward movement of the rack 40 (not illustrated in FIG. 4; refer to FIG. 2, for example) is prevented. As a result, forward and backward movement of the pulling wire 51 (not illustrated in FIG. 4; refer to FIG. 2, for example) is stopped. In this manner, a raising operation of the raising base 52 (not illustrated in FIG. 4; refer to FIG. 2, for example) along with the movement of the pulling wire 51 is stopped.

When the switching operation member 30A is rotated about the support shaft 38 in, for example, an arrow RC2 direction (clockwise direction; second direction) in FIG. 4, the pressing plate 37 moves in the arrow Z2 direction and is separated from the one surface of the rotation member 36. Accordingly, the pressing state of the rotation member 36 by the pressing plate 37 is released. As a result, rotation of the rotation member 36 is released. Simultaneously, forward and backward movement of the rack 40 is released. Accordingly, stopping of forward and backward movement of the pulling wire 51 is released. Accordingly, the pulling wire 51 moves in a predetermined direction (the arrow X1 direction refer to in FIG. 2) in the long-axis direction by the biasing force by the biasing force generation mechanism 31 (not illustrated in FIG. 4; refer to FIG. 2, for example). Raising operation of the raising base 52 starts along with the movement.

The switching mechanism 32A thus configured includes the pressing plate 37 having a surface that is pressed against the outer surface of the rotation member 36 upon receiving operational force by a finger of the endoscope operator in the first state. In this case, the pressing plate 37 prevents rotation operation of the rotation member 36 in the first state. Accordingly, the switching mechanism 32A restrains the biasing force by the biasing force generation mechanism 31.

Thus, similarly to the switching mechanism 32 in the above-described embodiment, the switching mechanism 32A can switch the first state and the second state upon receiving operational force by a finger of the endoscope operator.

In the above-described modification of the switching mechanism 32A, the pressing plate 37 has the tilt surface 37a. However, the switching mechanism 32A is not limited to the exemplary configuration.

For example, a tilt surface similar to the tilt surface 37a of the pressing plate 37 may be provided on the one surface of the rotation member 36.

The tilt surface 37a of the pressing plate 37 in the configuration of the above-described modification of the switching mechanism 32A may be replaced with a configuration in which surfaces at which a pressing plate and a rotation member face each other have shapes as follows. A rotation member 36 is configured to rotate about a central axis, and an engagement member 36a is in engagement with the rotation member 36, and the engagement member 36a is configured to move the wire in a long-axis direction of the operation portion 12 or insertion portion 11 when the rotation member 36 rotates about the central axis. The switching mechanism 32 includes a pressing member 37 having a pressing state in which a surface of the pressing member 37B is in contact with an outer surface of the rotation member to prevent rotation of the rotation member 36. At least one of the rotation member 36 and the pressing member 37 includes, at a location where the rotation member 36 and the pressing member 37 face each other, a ratchet mechanism that allows rotation of the rotation member 36 in a first direction and prevents rotation of the rotation member in a second direction.

Figure 5:
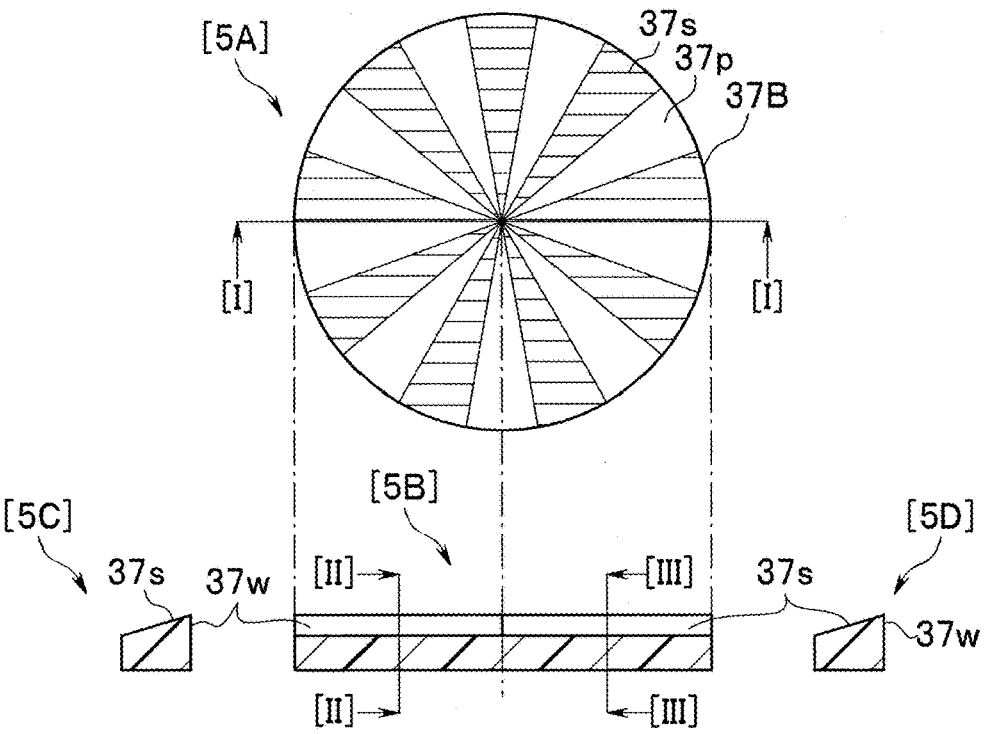
FIG. 5 is a diagram illustrating another modification of the switching mechanism in the endoscope according to the embodiment of the present disclosure.

FIG. 5 is a diagram of another modification of the switching mechanism, conceptually illustrating a shape of each of surfaces at which a pressing plate and a rotation member face each other. Note that in FIG. 5, reference sign [5A] denotes a plan view. In FIG. 5, reference sign [5B] denotes a cross-sectional view taken along a line [I]-[I]. In FIG. 5, reference sign [5C] denotes a cross-sectional view taken along a line [II]-[II]. In FIG. 5, reference sign [5D] denotes a cross-sectional view taken along a line [III]-[III]. In FIG. 5 with reference sign [5A], a hatched region indicates a slant surface.

Although FIG. 5 illustrates a surface shape of a pressing plate 37B, a surface shape of a rotation member corresponding to the pressing plate 37B is formed same and thus omitted in the illustration.

One surface of the pressing plate 37B facing the rotation member (not illustrated) is formed with a plurality of plane regions 37p and a plurality of ridged-shape protrusion portions 37s. In this case, the plane regions 37p and the ridged-shape protrusion portions 37s are alternately arranged in a circumferential direction.

The plurality of plane regions 37p are each formed in a substantially fan shape from a central point of the pressing plate 37B.

The plurality of ridged-shape protrusion portions 37s each have a section in a substantially right-triangle shape and each include a perpendicular wall surface 37w and a tilt surface 37s.

With such a configuration, when the pressing plate 37B is pressed against the rotation member, the ridged-shape protrusion portions are engaged, which prevents rotation of the rotation member. When the pressing plate 37B is separated from the rotation member, the engagement between the ridged-shape protrusion portions is released, which allows rotation of the rotation member.

Accordingly, with the switching mechanism in such a form, as well, it is possible to switch the first state and the second state upon receiving operational force by a finger of the endoscope operator.

In the endoscope 2 according to the above-described embodiment, the first link member 42 of the drive power transmission mechanism 34 and the rack 40 and the rack guide 41 of the raising-base lay-down operation mechanism 33 are each disposed at a predetermined angle relative to the wire guide 45 (the moving direction X of the pulling wire 51). However, disposition of the first link member 42 of the drive power transmission mechanism 34 and the rack 40 and the like of the raising-base lay-down operation mechanism 33 is not limited to the exemplary configuration.

Figure 6:
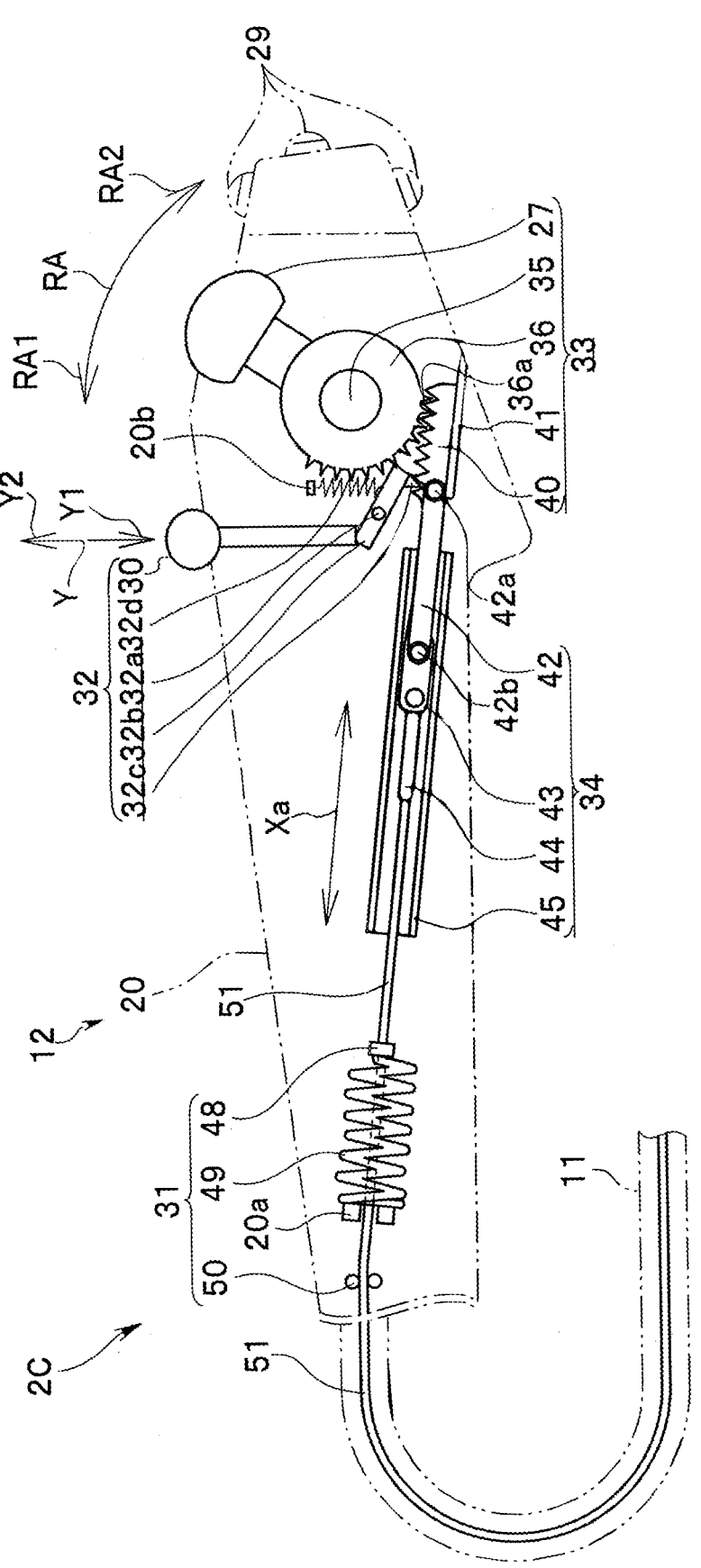
FIG. 6 is a schematic configuration diagram mainly illustrating the raising-base-related mechanism unit in a first modification of the endoscope according to the embodiment of the present disclosure.

For example, FIG. 6 is a schematic configuration diagram mainly illustrating raising-base-related mechanism units in a first modification of the endoscope according to the embodiment of the present disclosure.

In an endoscope 2C according to the first modification illustrated in FIG. 6, the first link member 42 of the drive power transmission mechanism 34 and the rack 40 and the rack guide 41 of the raising-base lay-down operation mechanism 33 are disposed substantially in parallel to the wire guide 45 (the moving direction X of the pulling wire 51) and the biasing force generation mechanism 31. Accordingly, the biasing force generation mechanism 31, the drive power transmission mechanism 34, and the raising-base lay-down operation mechanism 33 are substantially linearly formed. The other configuration is the same as in the above-described embodiment.

With such a configuration, in the endoscope 2C according to the first modification, the pulling wire 51 moves in an arrow Xa direction in FIG. 6. Note that, in this case, the moving direction of the pulling wire 51 is converted without interference at, for example, a part corresponding to the speed reduction member 50.

Accordingly, in the endoscope 2C according to the first modification, drive power of the pulling wire 51 being moved by the biasing force by the biasing force generation mechanism 31 can be efficiently transmitted to the raising-base lay-down operation mechanism 33 through the drive power transmission mechanism 34. In addition, drive power generated by operational force on the raising operation lever 27 can be efficiently transmitted from the raising-base lay-down operation mechanism 33 to the biasing force generation mechanism 31 through the drive power transmission mechanism 34.

In the endoscope 2 according to the above-described embodiment and the endoscope 2C according to the first modification of the above-described embodiment, the drive power transmission mechanism 34 is provided between the biasing force generation mechanism 31 and the raising-base lay-down operation mechanism 33. However, an endoscope of the present disclosure is not limited to the exemplary configuration.

Figure 7:
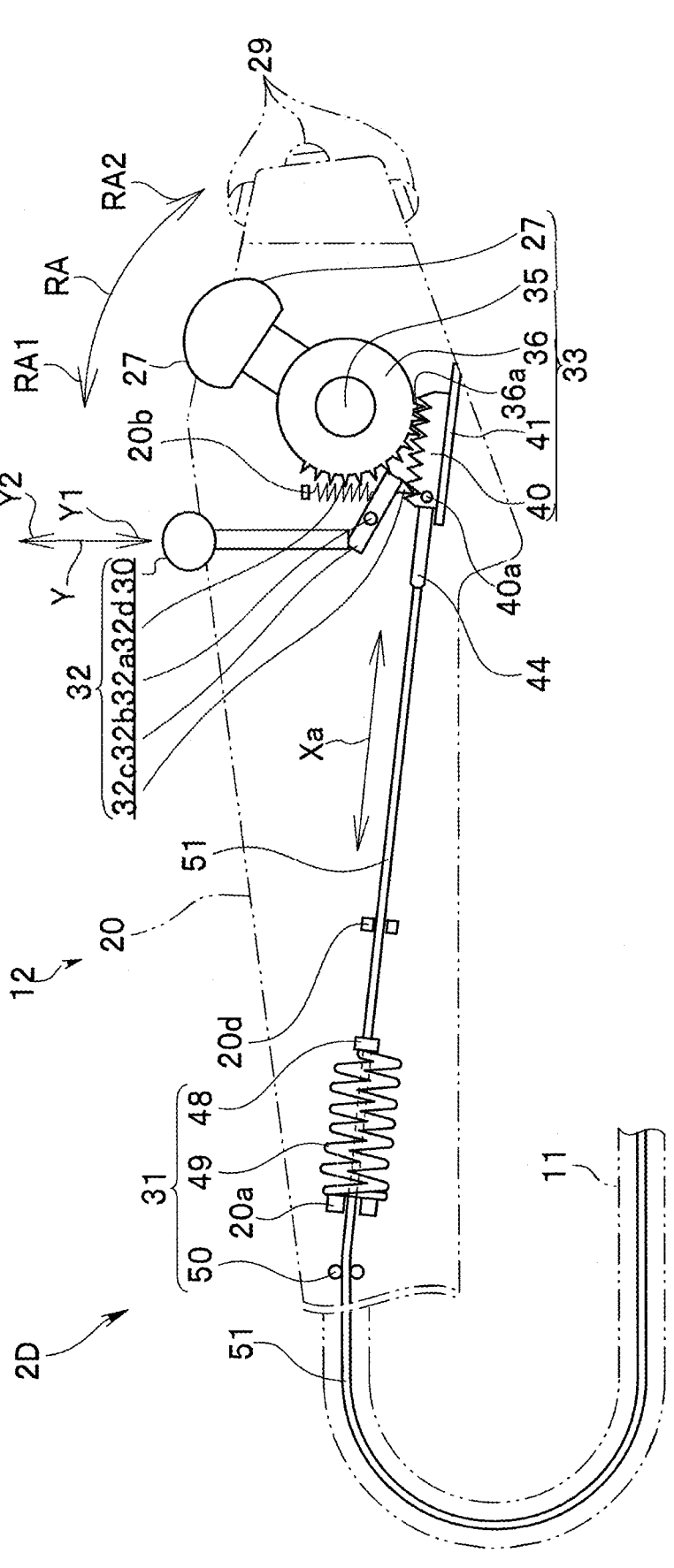
FIG. 7 is a schematic configuration diagram mainly illustrating the raising-base-related mechanism unit in a second modification of the endoscope according to the embodiment of the present disclosure.

For example, FIG. 7 is a schematic configuration diagram mainly illustrating raising-base-related mechanism units in a second modification of the endoscope according to the embodiment of the present disclosure.

In an endoscope 2D according to the second modification illustrated in FIG. 7, the drive power transmission mechanism 34 in the endoscope 2 according to the above-described embodiment and the endoscope 2C according to the first modification is omitted. Instead, an internal fixed part 20d of the operation portion 12 is provided as a position restricting portion for restricting movement of the pulling wire 51 when the biasing force generation member 49 is extended.

The one end of the wire coupling member 44 to which the other end of the pulling wire 51 is connected is connected to the rack 40. The wire coupling member 44 may have a predetermined flexibility in a direction intersecting a longitudinal axis of the wire 51 or may be pivotally supported to be freely rotatable through a link shaft 40a at a predetermined angle relative to the rack 40.

The pulling wire 51 is disposed extending in parallel to the rack 40 and the rack guide 41. Accordingly, the pulling wire 51 moves in the direction along the arrow Xa. In this case, similarly to the above-described first modification, the moving direction of the pulling wire 51 is converted without interference at a part corresponding to the speed reduction member 50. The other configuration is substantially the same as in the above-described embodiment and the first modification.

With such a configuration, it is possible to obtain effects substantially the same as effects of the above-described embodiment and the first modification although the drive power transmission mechanism 34 in the endoscope 2 according to the above-described embodiment and the endoscope 2C according to the first modification is omitted.

In the endoscope 2 according to the above-described embodiment, the gear 36a of the rotation member 36 and the gear train of the rack 40 in the raising-base lay-down operation mechanism 33 are constantly engaged with each other. With this configuration, the raising operation lever 27 inclines in the arrow RA1 direction in FIG. 2 when the switching mechanism 32 is switched from the first state to the second state and the pulling wire 51 is moved in the arrow X1 direction in FIG. 2 by the biasing force by the biasing force generation mechanism 31.

A third modification of the endoscope according to the embodiment of the present disclosure to be described next has a structure in which the raising operation lever 27 does not move when the switching mechanism 32 is switched from the first state to the second state and the raising base 52 is raised. The switching mechanism 32 includes a detent 32c connected to a lever 30, and in the first state, the detent 32c is engaged with the coupling unit 40 and, in the second state, the detent 32c is disengaged from the coupling unit 40.

FIGS. 8A to 8D and 9A to 9C are diagrams illustrating the third modification of the endoscope according to the embodiment of the present disclosure. FIGS. 8A to 8D and 9A to 9C illustrate a schematic configuration of an endoscope 2E according to the third modification and also effects of the endoscope 2E according to the third modification. Note that a basic configuration of the third modification is substantially the same as in the above-described embodiment. Accordingly, the third modification will be described in detail for any component different from the above-described embodiment, and any same component is denoted by the same reference sign and detailed description of the component is omitted.

In the endoscope 2E according to the third modification, the gear 36a of the rotation member 36 and the gear train of the rack 40 in the raising-base lay-down operation mechanism 33 are not engaged with each other in a normal state. Note that the normal state is a state in which no external operational force is applied to the raising-base lay-down operation mechanism 33 through the raising operation lever 27. The gear 36a of the rotation member 36 and the gear train of the rack 40 are engaged with each other when an amount of operational force in a predetermined direction is applied to the raising operation lever 27.

To achieve the non-engaged state, the endoscope 2E according to the third modification includes an urging member 39 (biasing member 39) that constantly applies biasing force in a predetermined direction (arrow Y3 direction in FIG. 8A) to the rotation member 36 in the raising-base lay-down operation mechanism 33.

The urging member 39 is formed of, for example, a contractive coil spring. One end of the urging member 39 is fixed to a predetermined site of the rotation member 36. The other end of the urging member 39 is fixed to an internal fixed part 20e of the operation portion 12.

With this configuration, the urging member 39 constantly urges the rotation member 36 in a direction (arrow Y3 direction in FIG. 8A) separating from the rack 40. Similarly to the above-described embodiment, the raising operation lever 27 is integrated with the rotation member 36. Accordingly, the gear 36a of the rotation member 36 and the gear train of the rack 40 are not engaged with each other (refer to FIG. 8A) in the normal state in which no external operational force is applied to the raising-base lay-down operation mechanism 33 through the raising operation lever 27.

Figures 9A, 9B, 9C:
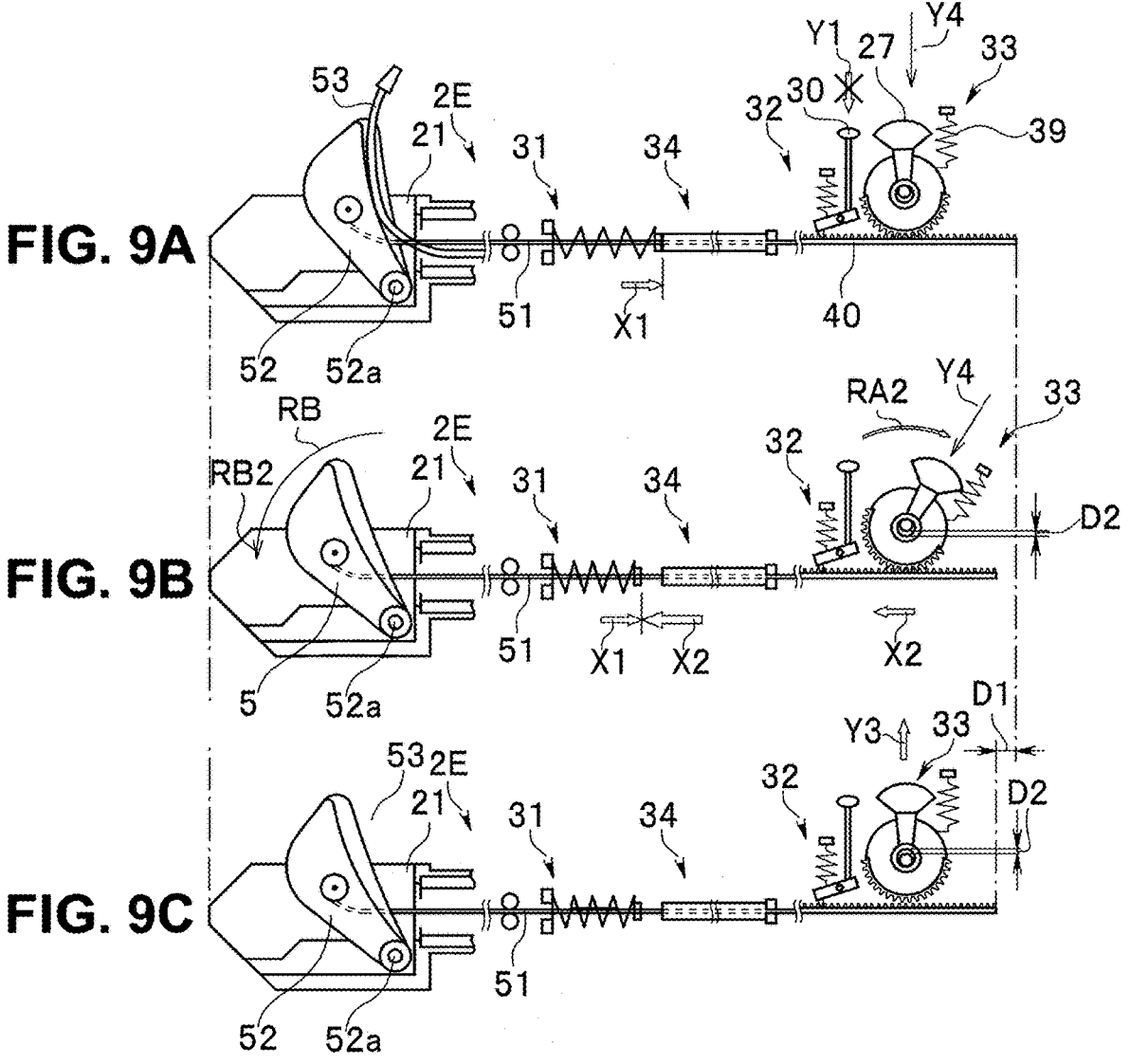
FIG. 9A is a diagram illustrating a second-half part of the configuration and the effect of the third modification of the endoscope according to the embodiment of the present disclosure.
FIG. 9B is a diagram illustrating the second-half part of the configuration and the effect of the third modification of the endoscope according to the embodiment of the present disclosure.
FIG. 9C is a diagram illustrating the second-half part of the configuration and the effect of the third modification of the endoscope according to the embodiment of the present disclosure.

The gear 36a of the rotation member 36 and the gear train of the rack 40 can be engaged with each other (refer to FIG. 9A) when the endoscope operator applies, to the raising operation lever 27 with a finger, operational force in an arrow Y4 direction in FIGS. 8D and 9A against biasing force by the urging member 39. Note that the operational force in the arrow Y4 direction is a direction along a long axis of the raising operation lever 27 and a direction in which the gear 36a of the rotation member 36 is engaged with the gear train of the rack 40. The other configuration is the same as in the above-described embodiment.

Note that, to avoid drawing complication and conceptualize configurations, FIGS. 8A to 8D and 9A to 9C illustrate that the biasing force generation mechanism 31, the drive power transmission mechanism 34, and the raising-base lay-down operation mechanism 33 are substantially linearly disposed. The illustration conceptually indicates a structure in which the biasing force by the biasing force generation mechanism 31 is transmitted to the raising-base lay-down operation mechanism 33 through the drive power transmission mechanism 34 by the pulling wire 51. Accordingly, the illustration is not different from configurations described in detail in the above-described embodiment and the modifications.

Effects of the endoscope 2E according to the third modification thus configured will be briefly described below. A state illustrated in FIG. 8A corresponds to the normal state before the endoscope 2E is used. In this state, the raising base 52 is in the laid-down state. The switching mechanism 32 is in the first state in which the lock click 32c and the gear train of the rack 40 are engaged with each other. The biasing force by the biasing force generation mechanism 31 is stored and suppressed. Accordingly, movement of the pulling wire 51 and raising operation of the raising base 52 are being stopped.

In this state, the endoscope operator performs a normal endoscope operation to insert the insertion portion 11 into a body cavity of a subject. Then, when the distal end portion 21 of the insertion portion 11 has reached near a target site at which a procedure is to be performed, the endoscope operator performs a normal endoscope operation to introduce the treatment instrument 53 through the forceps port 25 of the operation portion 12 and dispose the distal end of the treatment instrument 53 near the distal end portion 21. This state is illustrated in FIG. 8B.

In the state in FIG. 8B, the switching operation member 30 is operated by pressing the arrow Y1 direction in FIG. 8B. Upon the pressing operation, the switching mechanism 32 switches to the second state in which engagement between the lock click 32c and the gear train of the rack 40 is released. As a result, the biasing force by the biasing force generation mechanism 31 is released and the pulling wire 51 moves in the arrow X1 direction in FIG. 8C by a moving amount denoted by reference sign D1 in FIG. 8C. As the pulling wire 51 moves in the arrow X1 direction, the raising base 52 is rotated and raised in the arrow RB1 direction in FIG. 8D. In this case, the moving speed of the pulling wire 51 is suppressed by the effect of the speed reduction member 50. Accordingly, the raising base 52 is not abruptly raised. In this case, the gear 36a of the rotation member 36 and the gear train of the rack 40 are not engaged with each other by the biasing force by the urging member 39. Thus, the raising operation lever 27 does not move even when the pulling wire 51 is moved and the raising base 52 is in raising operation.

Simultaneously, due to the movement of the pulling wire 51, the rack 40 moves in the arrow X1 direction from a position illustrated in FIG. 8C to a position illustrated in FIG. 8D. In this case, the rack 40 moves by a moving amount denoted by reference sign D1 in FIG. 8D. In this manner, the leading direction of the treatment instrument 53 can be changed by raising the raising base 52.

In this state, the pressing operation on the switching operation member 30 in the arrow Y1 direction is released. As a result, the switching mechanism 32 switches to the first state in which the lock click 32c and the gear train of the rack 40 are engaged with each other (refer to FIG. 9A). Accordingly, the raised state of the raising base 52 is maintained. Then, treatment is performed by using the treatment instrument 53. The raised state of the raising base 52 is maintained during an operation in the treatment, and thus the endoscope operator does not need to perform an operation related to a raising operation and can focus on other bending operation and treatment instrument operation.

Subsequently, when the raised state of the raising base 52 becomes unnecessary since a procedure or the like ends, an operation for laying down the raising base 52 from a state illustrated in FIG. 9A is performed. Note that, before the operation is performed, for example, an operation to remove the treatment instrument 53 is performed.

First, in the state in FIG. 9A (note that the treatment instrument 53 is already removed), a pressing operation in the arrow Y4 direction in FIG. 9A is performed on the raising operation lever 27. Accordingly, the gear 36a of the rotation member 36 and the gear train of the rack 40 are engaged with each other. Then, the raising operation lever 27 is inclined in the arrow RA2 direction in FIG. 9B while the pressing operation on the raising operation lever 27 in the arrow Y4 direction is maintained. Accordingly, the rotation member 36 rotates in the clockwise direction about the main support shaft 35. As a result, the rotation member 36 moves the rack 40 in the arrow X2 direction in FIG. 9B. Note that, in this case, the switching mechanism 32 is in a state in which the lock click 32c and the gear train of the rack 40 are engaged with each other. However, in the third modification, although the switching mechanism 32 is in this state, movement of the rack 40 in the arrow X2 direction is allowed. Thus, an operation on the switching mechanism 32 is unnecessary in the third modification.

Accordingly, the raising-base lay-down operation mechanism 33 acts on the pulling wire 51 through the drive power transmission mechanism 34. Specifically, the pulling wire 51 moves in the arrow X2 direction against the biasing force by the biasing force generation mechanism 31 in the arrow X1 direction. The biasing force generation member 49 of the biasing force generation mechanism 31 is contracted along with the movement of the pulling wire 51 in the arrow X2 direction. In this case, the raising base 52 rotates by a predetermined amount in the arrow RB2 direction in FIG. 9B and is laid down by a predetermined amount.

The raising base 52 cannot be completely laid down by a single inclining operation on the raising operation lever 27 in the arrow RA2 direction in some cases. In such a case, the pressing operation on the raising operation lever 27 in the arrow Y4 direction is released. As a result, the raising operation lever 27 is moved in the arrow Y3 direction by the biasing force by the urging member 39. Accordingly, engagement between the gear 36a of the rotation member 36 and the gear train of the rack 40 is released. As a result, the rotation member 36 becomes freely rotatable and thus can be returned to a position illustrated in FIG. 9C. In this state, the operation in FIG. 9A and later are repeated. The switching mechanism 32 includes a detent 32 connected to a lever 30, and in the first state, the detent 32 is engaged with the coupling unit 40 and, in the second state, the detent 32 is disengaged from the coupling unit 40.

Then, when the raising base 52 has transitioned to the laid-down state illustrated in FIG. 8A, the operation on the raising operation lever 27 is released. In this case, the lock click 32c of the switching mechanism 32 and the gear train of the rack 40 are engaged with each other, thereby preventing movement of the pulling wire 51 in the arrow X1 direction. Accordingly, the laid-down state of the raising base 52 is maintained. Note that the transition to the laid-down state can be confirmed because the raising operation lever 27 becomes unable to be operated. Note that, in the above-described embodiment, the urging member 39 may be formed as a plate spring, a coil spring, or an axle spring made of an elastic material or the like, which is provided about the main support shaft 35 and constantly applies biasing force in a predetermined direction (the arrow Y3 direction in FIG. 8A) to the rotation member 36.

As described above, in the above-described third modification as well, it is possible to obtain the same effects as the effects of the above-described embodiment and the modifications. In addition, in the third modification, the raising operation lever 27 does not move during a raising operation of the raising base 52. Accordingly, it is possible to obtain more favorable operability of the endoscope.

The present disclosure is not limited to the above-described embodiment and may be modified and applied in various manners without departing from the gist of the disclosure. Disclosure at various kinds of stages is included in the above-described embodiment, and various kinds of disclosure can be extracted through appropriate combinations of a plurality of disclosed components. For example, some components may be deleted from among all components indicated in the above-described embodiment, and the remaining configuration from which the components are deleted may be extracted as a disclosure as long as the technical problem can be solved and effects of disclosure can be obtained. Moreover, constituent components in different embodiments may be combined as appropriate. The present disclosure is limited by the claims but not restricted by particular aspects of the claims.

Example 1. An endoscope comprising:
   a raising base provided on one end side of an insertion portion that is inserted into a subject;
   an operation portion coupled on another end side of the insertion portion and configured to operate the raising base;
   a transmission member configured to transmit drive power between the operation portion and the raising base;
   an urging force generation member connected to the transmission member and configured to constantly apply, to the transmission member, urging force in a direction of raising operation of the raising base;
   a switching mechanism provided at the operation portion and configured to switch between a first state and a second state, the first state being a state in which the urging force is restrained to stop raising operation of the raising base, the second state being a state in which the urging force is released to allow raising operation of the raising base; and
   a switching operation member configured to act on the switching mechanism to cause switching between the first state and the second state upon receiving operational force.

Example 2. The endoscope according to Example 1, further comprising:
   a raising-base lay-down operation mechanism provided at the operation portion and configured to cause transition of the raising base from a raised state to a laid-down state when operated against the urging force; and
   a second operation member configured to act on the raising-base lay-down operation mechanism to cause transition of the raising base from the raised state to the laid-down state upon receiving operational force.

Example 3. The endoscope according to Example 2, wherein
   the raising-base lay-down operation mechanism includes
      a rotation member configured to rotate about a support shaft, and
      an engagement member that is coupled to the transmission member, is engaged with the rotation member, and moves the transmission member in a long-axis direction by moving forward and backward in accordance with rotation of the rotation member, and
   the second operation member includes an operation lever configured to rotate the rotation member upon receiving the operational force.

Example 4. The endoscope according to Example 3, wherein the rotation member is provided with a gear, and the engagement member includes a rack that is engaged with the gear.

Example 5. The endoscope according to Example 4, wherein the switching mechanism includes a clutch configured to switch between the first state in which engagement is made with the gear or the rack and the second state in which the engagement is released.

Example 6. The endoscope according to Example 5, wherein the clutch is engaged with the gear or the rack to restrain the urging force in the first state and controls operation of the transmission member.

Example 7. The endoscope according to Example 1, wherein the transmission member is an elongated member connected to the raising base and extended to the operation portion, and the raising base is raised or laid down by being rotationally operated in accordance with forward and backward movement of the elongated member.

Example 8. The endoscope according to Example 1, wherein the switching mechanism includes a rack connected to the transmission member, and a clutch configured to switch between the first state in which engagement is made with the rack and the second state in which the engagement is released.

Example 9. The endoscope according to Example 1, further comprising:

a rotation member configured to rotate about a central axis; and an engagement member configured to move the transmission member in a long-axis direction by engaging with the rotation member, wherein the switching mechanism includes a pressing member having a surface that is pressed against an outer surface of the rotation member in the first state upon receiving operational force, and restrains the urging force by preventing rotational operation of the rotation member in the first state.

Example 10. The endoscope according to Example 9, wherein at least one of the rotation member and the pressing member includes, at a part where the rotation member and the pressing member face to each other, a ridged-shape protrusion that allows rotation of the rotation member in a forward direction and prevents rotation of the rotation member in an opposite direction.

Example 11. The endoscope according to Example 1, wherein the urging force generation member has one end connected to a fixed part of the operation portion and has another end fixed to the transmission member.

Example 12. The endoscope according to Example 1, further comprising a speed reduction member configured to reduce a speed at which the raising base is raised by urging force of the urging force generation member.

Example 13. The endoscope according to Example 12, wherein the speed reduction member includes a frictional member configured to apply frictional force to at least movement of the transmission member.

Example 14. The endoscope according to Example 1, wherein the endoscope is any of a duodenum endoscope, a biliary-tract endoscope, or an ultrasound endoscope including an ultrasound probe configured to transmit and receive ultrasound at a distal end portion of the insertion portion.

Example 15. The endoscope according to Example 14, wherein the endoscope is a single-use endoscope that is discarded after used once.

What is claimed is:

1. An endoscope, comprising:

an insertion portion;

a raising base provided at a distal end of the insertion portion;

a wire configured to move in a raising direction to raise the raising base;

a biasing element attached to the wire and configured to apply to the wire a first biasing force in the raising direction; and an operation portion coupled to a proximal end of the insertion portion, the operation portion including a switching mechanism having a first state and a second state, wherein the switching mechanism is configured to switch between the first state and the second state, wherein, in the first state, the switching mechanism prevents the first biasing force from moving the wire in the raising direction and, in the second state, the switching mechanism allows the first biasing force to move the wire in the raising direction, and wherein a proximal end of the biasing element is connected to the wire.

2. The endoscope according to claim 1, wherein the operation portion includes a raising base operator and a coupling unit, wherein the raising base operator is movable between a first position and a second position, wherein the coupling unit is attached to the wire and the raising base operator is in engagement with the coupling unit, and wherein, when the switching mechanism is in the second state, movement of the raising base operator toward the first position moves the wire in a direction opposite of the raising direction.

3. The endoscope according to claim 2, wherein the raising base operator includes a first rotation member configured to rotate about a shaft, and the coupling unit includes an engagement member, wherein engagement of the raising base operator with the coupling unit includes engagement by a surface of the first rotation member with the engagement member, and wherein movement of the raising base operator between the first position and the second position includes rotation of the first rotation member.

4. The endoscope according to claim 3, wherein the surface of the first rotation member includes a first plurality of teeth and defines a pinion, wherein the engagement member includes a second plurality of teeth and defines a rack, and the pinion and the rack cooperate in a rack and pinion structure.

5. The endoscope according to claim 4, wherein the switching mechanism includes a clutch movable between an engaged state and a non-engaged state, and wherein, in the engaged state, the clutch engages with the pinion or the rack and, in the non-engaged state, the clutch is not engaged with the pinion or the rack.

6. The endoscope according to claim 5, wherein, when the switching mechanism is in the first state, the clutch is in the engaged state.

7. The endoscope according to claim 3, further including a rotation-member biasing element, wherein the rotation-member biasing element applies a second biasing force to the first rotation member to bias the engagement between the first rotation member and the engagement member.

8. The endoscope according to claim 7, wherein a first end of the rotation-member biasing element is fixed to the first rotation member and a second end of the rotation-member biasing element is fixed to an internal surface of the operation portion.

9. The endoscope according to claim 3, wherein the switching mechanism includes an engagement-member biasing element and a locking member, and wherein the engagement-member biasing element applies a third biasing force to the switching mechanism to bias an engagement between the locking member and the engagement member.

10. The endoscope according to claim 9, wherein a first end of the engagement-member biasing element is fixed to the switching mechanism and a second end of the engagement-member biasing element is fixed to an internal surface of the operation portion.

11. The endoscope according to claim 2, wherein the switching mechanism includes a detent connected to a lever, and wherein, in the first state, the detent is engaged with the coupling unit and, in the second state, the detent is disengaged from the coupling unit.

12. The endoscope according to claim 1, wherein a first end of the wire is connected to the raising base and the wire extends from the raising base to the operation portion, and wherein the raising base is raised by movement of the wire in the raising direction and the raising base is lowered by movement of the wire in a direction opposite of the raising direction.

13. The endoscope according to claim 1, wherein the switching mechanism includes:

a rack connected to the wire, and a clutch configured to switch between an engaged state and a non-engaged state, wherein, in the engaged state, the clutch engages with the rack and, in the non-engaged state, the clutch is not engaged with the rack.

14. The endoscope according to claim 1, further comprising:

a first rotation member configured to rotate about a central axis; and an engagement member in engagement with the first rotation member, wherein the engagement member is configured to move the wire in a long-axis direction when the first rotation member rotates about the central axis, wherein the switching mechanism includes a pressing member having a pressing state in which a surface of the pressing member is in contact with an outer surface of the first rotation member to prevent rotation of the first rotation member.

15. The endoscope according to claim 14, wherein at least one of the first rotation member and the pressing member includes, at a location where the first rotation member and the pressing member face each other, a ratchet that allows rotation of the first rotation member in a first direction and prevents rotation of the first rotation member in a second direction.

16. The endoscope according to claim 1, further comprising a speed reduction member configured to reduce a speed at which the raising base is raised by the first biasing force of the biasing element.

17. The endoscope according to claim 16, wherein the speed reduction member includes a frictional member configured to apply a frictional force to the wire.

18. The endoscope according to claim 1, wherein the endoscope is a single-use endoscope, a duodenum endoscope, a biliary-tract endoscope, or an ultrasound endoscope including an ultrasound probe configured to transmit and receive ultrasound at a distal end portion of the insertion portion.

19. The endoscope according to claim 1, wherein a distal end of the biasing element is supported by a part of the operation portion.

* * * * *